United States Patent [19]

Eggler et al.

[11] Patent Number: 4,703,052

[45] Date of Patent: Oct. 27, 1987

[54] HYPOGLYCEMIC THIAZOLIDINEDIONES

[75] Inventors: James F. Eggler, Stongington; Gerald F. Holland, Old Lyme; Mickael R. Johnson, Gales Ferry; Robert A. Volkmann, Ledyard, all of Conn.

[73] Assignee: Pfizer Inc., New York, N.Y.

[21] Appl. No.: 10,081

[22] PCT Filed: May 21, 1985

[86] PCT No.: PCT/US85/00962

§ 371 Date: Dec. 29, 1986

§ 102(e) Date: Dec. 29, 1986

[51] Int. Cl.$^4$ .............. C07D 417/10; A61K 31/425
[52] U.S. Cl. ...................... 514/337; 514/369; 546/246; 546/274; 548/183
[58] Field of Search ............... 548/183; 546/269, 274; 514/337, 369

[56] References Cited

U.S. PATENT DOCUMENTS

4,461,902 7/1984 Kawamatsu .................. 548/183
4,572,912 2/1986 Yoshioka ...................... 514/369

FOREIGN PATENT DOCUMENTS

8203 2/1980 European Pat. Off. .
84926 8/1983 European Pat. Off. .
139421 5/1985 European Pat. Off. .

*Primary Examiner*—Robert Gerstl
*Attorney, Agent, or Firm*—Peter C. Richardson; Albert E. Frost; Robert K. Blackwood

[57] ABSTRACT

Hypoglycemic 2,3-dihydro-5-benzo[b]furanyl-2,3-dihydro-5-benzo[b]thienyl-, 3,4-dihydro(2H)-6-benzopyranyl- and 6-thiochromanyl-thiazolidine-2,4-diones and pharmaceutically acceptable salts thereof, method for their use in treatment of hyperglycemic animals and pharmaceutical compositions containing them.

19 Claims, No Drawings

HYPOGLYCEMIC THIAZOLIDINEDIONES

TECHNICAL FIELD

The present invention relates to certain compounds of the formula

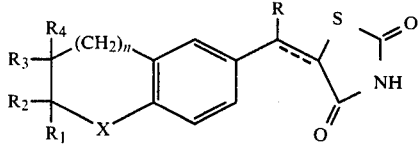

having utility as hypoglycemic agents, methods for their use and pharmaceutical compositions containing them.

BACKGROUND ART

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily, usually self, injection. Determination of the proper dosage of insulin requires frequent estimations of the sugar in the urine or in the blood. The administration of an excess dose of insulin causes hypoglycemia, with effects ranging from mild abnormalities in blood glucose to coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

In addition to the hypoglycemic agents cited above, a variety of other compounds have been reported to possess this type of activity, as reviewed recently by Blank [Burger's Medicinal Chemistry, Fourth Edition, Part II, John Wiley and Sons, N.Y. (1979), pp. 1057–1080].

U.S. Pat. No. 4,342,771 discloses a class of oxazolidinedione hypoglycemic agents of the general formula

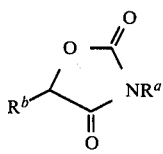

where $R^a$ is H or certain acyl groups and $R^b$ is certain mono- or bicyclic heterocyclic groups.

European Patent Application No. 117,035 discloses a group of 5-phenylthiazolidine-2,4-dione hypoglycemic agents of the formula

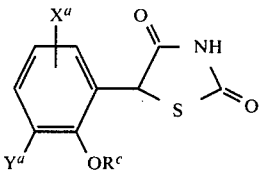

where $R^c$ is lower alkyl, $X^a$ is F, Cl or Br and $Y^a$ is H, Cl, lower alkyl or lower alkoxy.

U.S. Pat. No. 4,461,902 discloses certain 5-[(4-cyclohexylmethoxyphenyl)methyl]thiazolidine-2,4-dione hypoglycemic agents of the formula

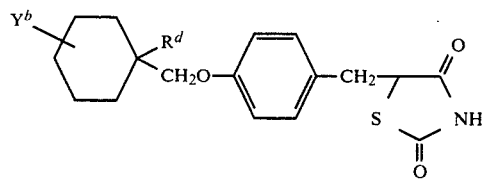

where $R^d$ is H or lower alkyl and $Y^b$ is an oxo or hydroxy group.

DISCLOSURE OF INVENTION

The present invention relates to compounds of the formula

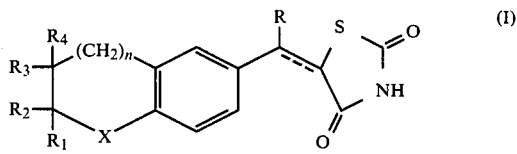

or a pharmaceutically acceptable cationic salt thereof, wherein the broken line is a bond or no bond, n is zero, 1, or 2; X is O, S,

$CH_2$, $C=O$, $CHOH$ or $NR_5$ where $R_5$ is H, formyl, $(C_2-C_5)$alkanoyl, benzyloxycarbonyl, $CO(CH_2)_xC_6H_5$ where x is an integer from 1 to 3, $(C_1-C_6)$alkyl, said alkyl optionally substituted by HO, Cl, Br, $OCH_3$, phenyl or $COOR_6$ where $R_6$ is $(C_1-C_4)$alkyl; R is H, $CH_3$ or $C_2H_5$; when taken separately, $R_1$ is H, $(C_5-C_7)$cycloalkyl, $(C_6-C_8)$methylsubstituted cycloalkyl, pyridyl, thienyl, furyl, naphthyl, p-biphenylyl, tetrahydrofuranyl, tetrahydrothienyl, tetrahydropyranyl, $C_6H_4W_2$ or alk-$W_1$ and alk is $(C_1-C_6)$alkylene, ethylidene or isopropylidene; $W_1$ is H, OH, $(C_1-C_4)$alkoxy, $(C_1-C_4)$thioalkyl, pyridyl, furyl, thienyl, tetrahydrofuryl, tetrahydrothienyl, naphthyl, $(C_5-C_7)$cycloalkyl or $C_6H_4W_2$ and $W_2$ is H, OH, F, Cl, Br, $(C_1-C_4)$alkyl, $(C_1-C_4)$alkoxy or $(C_1-C_4)$thioalkyl; $R_2$ is H or $CH_3$, $R_3$ is H, $(C_1-C_6)$alkyl, $C_6H_4W_2$ or benzyl; and $R_4$ is H;

where $R_1$ and $R_2$ are taken together they form $(C_4-C_6)$ alkylene and $R_3$ and $R_4$ are each H;

where $R_3$ and $R_4$ are taken together they form $(C_4-C_6)$ )alkylene and $R_1$ and $R_2$ are each H; and when $R_2$ and $R_3$ are taken together they are $(C_3-C_4)$alkylene and $R_1$ and $R_4$ are each H.

Preferred compounds are those wherein the broken line is no bond and R is H. Preferred values for $R_1$, $R_2$, $R_3$ and $R_4$ are $R_2$, $R_3$ and $R_4$ are each H and $R_1$ is H, cyclohexyl, $C_6H_4W_2$ or alk-$W_1$ where alk is $(C_1-C_4)$alkylene, ethylidene or isopropylidene; $W_1$ is H, OH, $(C_1-C_4)$alkoxy, cyclohexyl or $C_6H_4W_2$ and $W_2$ is H, F, Cl, Br, $CH_3$ or $CH_3O$. Preferred values of n are zero or 1. Preferred values of X are O, S,

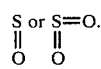

The compounds of the invention are useful as hypoglycemic agents and are mechanistically distinct from known hypoglycemics (the sulfonylureas) currently employed in diabetic therapy. Preferred invention compounds because of their excellent hypoglycemic activity in mammals are 5-[(2-benzyl-2,3-dihydrobenzofuran-5-yl)methyl]thiazolidine-2,4-dione and 5-[(2-benzyl-3,4-dihydro-2H-benzopyran-6-yl)methyl]thiazolidine-2,4-dione or a pharmaceutically acceptable cationic salt thereof.

The expression "pharmaceutically acceptable cationic salts" is intended to define such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol), procaine, etc. An especially preferred such salt is the sodium salt.

Mixtures of optically active isomers partially or completely optically resolved isomers of the compounds claimed herein are within the scope of the present invention.

Also embraced by the present invention are pharmaceutical compositions for use in treating a hyperglycemic mammal which comprises a blood glucose lowering amount of a compound of formula (I) and a pharmaceutically acceptable carrier. The invention further comprises a method of lowering blood glucose in a hyperglycemic mammal which comprises administering to a mammal in need of such treatment a blood glucose lowering effective amount of a compound of formula (I).

The compounds of formula (I) contain asymmetric centers at the 2-position, when $R_1$ and $R_2$ are different, and at the 3-position, when $R_3$ and $R_4$ are different. The compounds of formula (I) wherein the broken line is no bond have additional asymmetric centers at the R-bearing carbon atom linking the two rings, when R is methyl or ethyl; and at the 5-carbon of the thiazolidinedione group. Among the enantiomers of a given compound, one will ordinarily be favored over the others and the racemates because of its greater activity. The present invention is considered to be embracive of the racemates, diastereomeric mixtures, the pure enantiomers and diastereomers of the compounds of formula (I), the utility of which is determined by the biological evaluations described below.

DETAILED DESCRIPTION

The compounds of the invention are prepared, for example, by the method of Synthetic Scheme A, below.

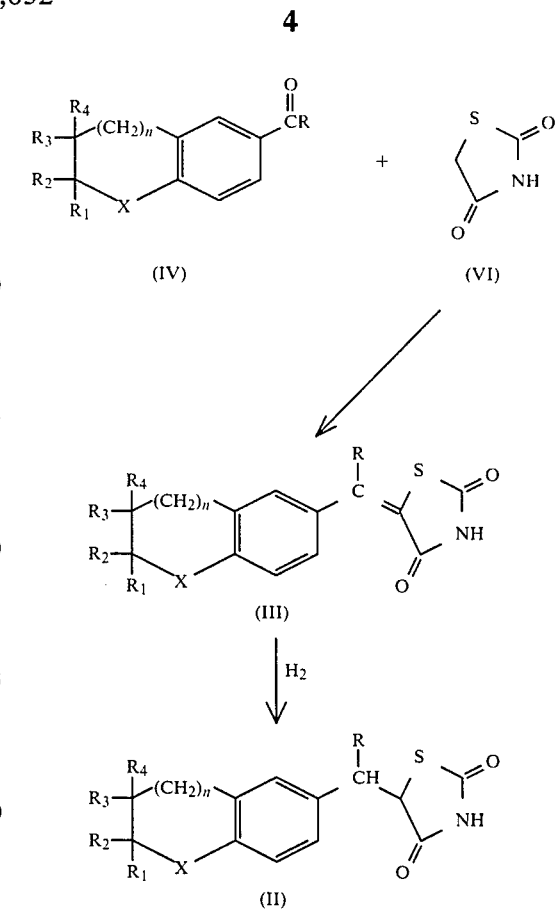

In the first step, approximately equimolar amounts of the reactant (IV), wherein n, R, $R_1-R_4$ and X are as defined above, and thiazolidinedione (VI) are heated in the presence of a mild base to provide the olefin of formula (III). While this step may be carried out in the presence of a reaction inert solvent, it is preferably carried out in the absence of solvent at a temperature which is sufficiently high to cause at least partial melting of the reaction mixture. A preferred such temperature is in the range of from 100° to 250° C., and especially preferred is a temperature of from 140° to 200° C.

Examples of suitable mild bases for the above reaction include the alkali metal and alkaline earth salts of weak acids such as the $(C_1-C_{12})$alkyl carboxylic acids and benzoic acid; alkali metal and alkaline earth carbonates and bicarbonates such as calcium carbonate, magnesium carbonate, potassium bicarbonate; and tertiary amines such as pyridine, N-methylmorpholine, N-ethylpiperidine and the like. An especially preferred mild base is sodium acetate for reasons of economy and efficiency.

In a typical such reaction the aldehyde or ketone starting material (IV) and thiazolidinedione (VI) are combined in approximately equimolar amounts with a molar excess, preferably a 2-4 fold molar excess, of anhydrous sodium acetate and the mixture is heated at a temperature high enough to effect melting, at which temperature the reaction is substantially complete in from about 5 to 60 minutes. The desired olefin of formula (III) is then isolated, for example, by mixing with water and filtration, to obtain the crude product, which is purified, if desired, e.g. by crystallization or by standard chromatographic methods.

The olefinic products of formula (III) are active hypoglycemic agents and also serve as intermediates for preparation of the corresponding reduced compounds of formula (II). While the reduction of the above olefins may be carried out by employing a wide variety of reducing agents which are known to reduce carbon-to-carbon double bonds, the preferred method employs hydrogen in the presence of a noble metal catalyst. Typically, the hydrogenation is carried out in the presence of a reaction inert solvent.

When the reduction step is carried out employing hydrogen in the presence of a noble metal catalyst, a convenient method for carrying out this transformation is to stir or shake a solution of a compound of the formula (III) under an atmosphere of hydrogen, or hydrogen mixed with an inert diluent such as nitrogen, in the presence of a noble metal hydrogenation catalyst. Suitable solvents for this reaction are those which substantially dissolve the starting compound of the formula (III) but which do not themselves suffer hydrogenation or hydrogenolysis. Examples of such solvents include ethers such as diethyl ether, tetrahydrofuran, dioxane and 1,2-dimethoxyethane; low molecular weight esters such as ethyl acetate and butyl acetate; tertiary amides such as N,N-dimethylformamide, N,N-dimethylacetamide and N-methylpyrrolidone; and lower alkyl carboxylic acids such as formic, acetic, propionic and isobutyric acid. An especially preferred such solvent is glacial acetic acid.

Introduction of the hydrogen gas into the reaction medium is usually accomplished by carrying out the reaction in a sealed vessel, containing the compound of formula (III), the solvent, the catalyst and the hydrogen. The pressure inside the reaction vessel can vary from about 1 to about 100 kg/cm$^2$. The preferred pressure range, when the atmosphere inside the reaction vessel is substantially pure hydrogen, is from about 2 to about 5 kg/cm$^2$. The hydrogenation is generally run at a temperature of from about 0° to about 60° C., and preferably from about 25° to about 50° C. Utilizing the preferred temperature and pressure values, hydrogenation generally takes place in a few hours, e.g. from about 2 hours to about 20 hours. The preferred noble metal catalysts used in this hydrogenation reaction are the type of agents known in the art for this kind of transformation, for example, nickel, palladium, platinum and rhodium. A palladium catalyst is preferred because such catalysts are not readily poisoned by sulfur. The catalyst is usually present in an amount from about 0.01 to about 25 weight-percent, and preferably from about 0.1 to about 10 weight-percent, based on the compound of formula (III). It is often convenient to suspend the catalyst on an inert support; a particularly convenient catalyst is palladium suspended on an inert support such as carbon.

When the hydrogenation is substantially complete, the desired product of formula (II) is then isolated by standard methods, e.g. the catalyst is removed by filtration, the solvent evaporated and the product purified, if desired, by well known methods such as crystallization or by chromatography.

A preferred method for reduction of the compounds of formula (III) where X is S, to the corresponding compounds of formula (II), is by means of a metal-acid couple which produces hydrogen in situ. A preferred such metal-acid couple for this reduction is zinc and acetic acid.

The pharmaceutically acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and addition of a non-solvent.

2,4-Thiazolidinedione (VI) is commercially available. The aldehydes and ketones of formula (IV) are prepared by a variety of well known methods, for example, by mild oxidation of the corresponding primary or secondary alcohol with reagents such as manganese dioxide or chromic acid under conditions known to produce aldehydes from primary alcohols and ketones from secondary alcohols; reaction of the appropriate dihydrofuran, 3,4-dihydro-2H-benzopyran, dihydrobenzothiophene or thiachroman with titanium tetrachloride in methylene chloride with 1,1-dichloromethylmethyl ether; reaction of the corresponding bromine substituted bicyclic hydrocarbon with n-butyl lithium followed by N,N-dimethylformamide at −80° to −70° C.; and other methods well known in the art.

When the above-mentioned reaction with titanium tetrachloride and 1,1-dichloromethylmethyl ether is carried out with certain 2-substituted dihydrobenzofurans in which the 2-position is substituted by a tertiary carbon atom bearing a phenyl group, the predominant reaction has been found to be a ring expansion to form a 6-formyl-3-phenyl, 2,2-disubstituted-3,4-dihydro-2H-benzopyran.

The requisite 2,3-dihydrobenzofurans, 2,3-dihydrobenzothiophenes, chromans, thiochromans, tetrahydrobenzooxepins and tetrahydrobenzothiepins, as well as the corresponding bromo-substituted and hydroxyalkyl-substituted compounds, described above as precursors of the starting aldehydes and ketones of formula (IV), are prepared by a variety of methods known in the art and illustrated in the Preparations, below.

The reactions employed to prepare the compounds of this invention can generally be monitored by standard tlc methods, employing commercially available plates. Suitable eluants are common solvents such as chloroform, ethyl acetate or hexane or suitable combinations thereof which will differentiate starting materials, products, by-products, and in some cases intermediates. Applying these methods, which are well known in the art, will permit further improvement in the methodology of the specific examples detailed hereinafter, e.g. the selection of more optimal reaction times and temperatures, as well as aid in the selection of optimal processes.

The thiazolidine-2,4-diones of the present invention are readily adapted to clinical use as antidiabetic agents. The activity required for this clinical use is defined by the test for hypoglycemic effect in ob/ob mice by the following procedure:

Six to eight week old C57 BL/6J-ob/ob mice (obtained from Jackson Laboratory, Bar Harbor, Maine) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (50 mg/kg) or vehicle. All drugs were administered in a vehicle consisting of 1.0% (v/v) polysorbate 80 (e.g. Tween 80, a registered trademark of ICI America, Inc.) in water with no pH adjustment. Animals were bled daily (via the ocular route) for blood metabolite levels just prior to oral administration of the test compound. The weight of each animal was recorded on days 1, 3 and 5 of the treatment. The freshly collected samples (125 microliters in 330 microliter tubes) were centrifuged for two minutes at 10,000 xg at room temperature. A 50 microliter sample was analyzed for glucose, for example, by the ABA 200 Bichromatic Analyzer*, using the A-gent* glucose UV reagent system+(hexokinase method) using 20, 60 and 100 mg/dl standards. Plasma glucose was then calculated by the equation, Plasma glucose (mg/dl) = Sample value $\times 5 \times 1.67 = 8.35 \times$ Sample value where 5 is the dilution factor and 1.67 is the plasma hematocrit adjustment (assuming the hematocrit is 40%).

*A registered trademark of Abbott Laboratories, Diagnostics Division, 820 Mission Street, So. Pasadena, CA 91030.
+A modification of the method of Richterich and Dauwalder, Schweizerische Medizinische Wochenschrift, 101, 860 (1971).

The thiazolidine-2,4-diones of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously, or intramuscularly, with intramuscular administration being preferred in man.

The present invention is illustrated by the following examples. However, it should be understood that the invention is not limited to the specific details of these examples. Proton magnetic resonance spectra were measured at 60, 90, 250 or 300 MHz for solutions in deuterochloroform ($CDCl_3$), deuterium oxide ($D_2O$), perdeutero acetone ($CD_3COCD_3$) or perdeutero dimethyl sulfoxide (DMSO-$d_6$) and peak positions are expressed in parts per million (ppm) downfield from tetramethylsilane. The following abbreviations are used: s, singlet; d, doublet; dd, doublet of doublets; t, triplet; q, quartet; m, multiplet; b, broad.

EXAMPLE 1

General Method A for Preparation of Aldehydes (IV), R=H, is illustrated below:

5-Formyl-2,3-dihydrobenzofuran

A solution of 9.4 ml (83.4 mmol) 2,3-dihydrobenzofuran in 250 ml methylene dichloride was cooled under nitrogen to 0° to −5° C. and 18 ml (167 mmole) titanium tetrachloride was added dropwise at 0° C. The resulting brown mixture was stirred 10 minutes and 8.3 ml (91.6 mmole) 1,1-dichloromethylmethyl ether was then added dropwise at 0° C. During this addition the reaction mixture became dark red in color. The mixture was allowed to warm to room temperature, stirred for 2 hours and poured slowly into a 2 liter beaker containing 700 ml saturated aqueous sodium bicarbonate solution The resulting mixture was filtered through diatomaceous earth and the solids washed with methylene dichloride. The separated organic layer was dried ($Na_2SO_4$) and the solvent evaporated to afford a residual oil, 10 g, (81%) which appeared homogeneous on silica gel thin-layer chromatography (TLC), eluting with an ethyl acetate/hexane/5% acetic acid, 1:5:5 by volume. Mass spectrum (m/e): 148 (M+), 147, 119.

EXAMPLE 2

The following aldehydes (IV) were also prepared by General Method A.

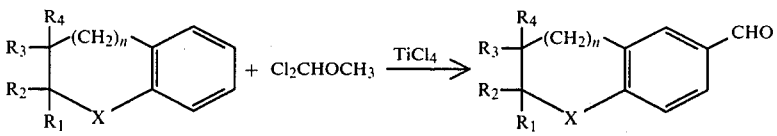

(IV)

| n | X | $R_1$ | $R_2$ | $R_3$ | $R_4$ | (%) Yield | Physical Properties |
|---|---|---|---|---|---|---|---|
| 0 | O | n-butyl | H | H | H | 97 | oil, $^1$H—NMR(CDCl$_3$)ppm(delta): 9.7. |
| 0 | O | 4-FC$_6$H$_4$CH$_2$ | H | H | H | 39$^{(a)}$ | m.p. 82–85° C.; IR (KBr)cm$^{-1}$: 1687 (s), 1676 (s), 1605 (s). |
| 0 | O | 2-FC$_6$H$_4$CH$_2$ | H | H | H | 49$^{(a)}$ | oil, M.S. 256 (M+). |
| 0 | O | (tetrahydropyranyl) | H | H | H | 58 | m.p. 107–111° C. |
| 0 | O | C$_6$H$_{11}$ | H | H | H | 33$^{(a)}$ | m.p. 91–93° C.; M.S. 230 (M+); IR(KBr)cm$^{-1}$: 2768, 2648, 1719, 1676, 1665, 1603, 1390. |
| 0 | O | C$_6$H$_5$CH$_2$ | H | H | H | 44.5$^{(a)}$ | oil, M.S. 244 (M+). |
| 0 | O | (1-methylcyclohexyl) | H | H | H | 59$^{(a)}$ | m.p. 53–56° C.; M.S. 244 (M+). |
| 0 | O | H | H | C$_6$H$_5$ | H | 72 | oil, $^1$H—NMR(CDCl$_3$)ppm(delta): 9.7. |
| 0 | O | H | H | C$_6$H$_4$CH$_2$ | H | 99 | oil, $^1$H—NMR(CDCl$_3$)ppm(delta): 9.8 (d), 10.2 (s). |
| 1 | O | H | H | spiro-cyclohexyl | H | 47$^{(a)}$ | viscous oil. |
| 0 | S | C$_6$H$_5$CH$_2$ | H | H | H | 93$^{(b,c)}$ | oil. |
| 0 | S | CH$_3$ | H | H | H | 79 | oil. |
| 0 | S | H | H | H | H | 36$^{(b)}$ | yellow oil. |
| 1 | S | H | H | H | H | — | — |

$^{(a)}$After purification of crude product by silica gel chromatography to separate it from the 7-formyl isomer.
$^{(b)}$Crude yield, contains 7-formyl isomer.
$^{(c)}$Reaction carried out at −5° C.

EXAMPLE 3

6-Formyl-2,2-dimethyl-3-phenyl-3,4-dihydro-2H-benzopyran

To a solution of 4.6 g (20 mmole) 2-(2-phenylpropan-2-yl)-2,3-dihydrobenzofuran in 75 ml methylene dichloride, under nitrogen, was cooled to 0° C. and 7.6 g (40 mmole) titanium tetrachloride was added in one portion, followed by dropwise addition of 2.5 g (22 mmole) dichloromethylmethyl ether. The resulting mixture was stirred at 0° C. for 45 minutes and poured into 100 ml water. The mixture was stirred for ten minutes, extracted three times with 125 ml portions of ethyl acetate. The combined extracts were washed twice with brine, dried (MgSO$_4$) and the solvent evaporated in vacuo to provide an amber viscous oil, 5.3 g (100%), which was shown to be a mixture of isomeric aldehydes by NMR. The oil was flash chromatographed on a 60 mm column packed with 18 cm of silica gel, eluting with 10:1 hexane/ethyl ether. Collection of like product fractions and evaporation of solvent gave product A, 1.7 g, m.p. 88°–92° C. and product B, 2.1 g as an oil. The latter product was identified as the title compound by NMR spectroscopy.

Product A is the 8-Formyl isomer of the title compound.

EXAMPLE 4

General Method B for Preparation of Aldehyde Precursors of Formula (IV) by oxidation of corresponding primary alcohol 5-Formyl-2-methyl-2,3-dihydrobenzofuran To a magnetically stirred solution of 680 mg (4.14 mmole) 5-hydroxymethyl-2-methyl-2,3-dihydrobenzofuran in 100 ml methylene dichloride was added 5.44 g manganese dioxide in one portion and the mixture stirred at room temperature overnight or until the reaction was complete as evidenced by thin-layer chromatography. The mixture was then filtered and the solvent evaporated to provide the title compound in quantitative yield. $^1$H-NMR(CDCl$_3$)ppm(delta): 1.6 (d, 3H), 2.7–3.6 (m, 1H), 5.1 (m, 2H), 6.8 (d, 1H), 7.6 (m, 2H), 9.8 (s, 1H).

EXAMPLE 5

Similarly, the approriate primary alcohol precursors were oxidized to the corresponding aldehydes of formula (IV) by the procedure of Example 4.

(IV, R_2,R_3,R_4 = H)

Structure: aromatic ring with -(CH_2)_n-, X, R_1 substituents and CHO group.

| n | X | R¹ | (%) Yield | ¹H—NMR(CDCl₃)ppm(delta): |
|---|---|---|---|---|
| 0 | O | CH₃OCH₂ | 95 oil | 3.2 (m, 2H), 3.4 (s, 3H), 3.6 (d, 2H), 5.08 (m, 1H), 6.8 (d, 1H), 7.6 (m, 2H), 10.2 (s, 1H). |
| 0 | O | CH₂OH | 95 | single peak at 9.8. no band at 4.6 (CH₂OH). |
| 1 | O | H | 100 (crude) | 9.8 (s, 1H). |
| 2 | O | H | 92 | oil, 9.8 (s, 1H). |

EXAMPLE 6

General Method C for Preparation of Aldehyde Precursors of Formula (IV) by reaction of n-butyl lithium and DMF with bromide.

2-Benzyl-5-formyl-2,3-dihydrobenzofuran

A. 2-Benzyl-5-bromo-2,3-dihydrobenzofuran

A solution of 2-benzyl-2,3-dihydrobenzofuran (1.9 g, 9 mmole) in 25 ml carbon tetrachloride was cooled to 0° C. and a solution of 0.46 ml (9 mmole) bromine in 5 ml carbon tetrachloride was added at 0° C. The mixture was warmed to room temperature, washed with water, sodium bicarbonate solution, and water again. The solvent was then evaporated to afford 2.5 g of crude product which was purified by column chromatography on silica gel, eluting with hexane to afford 1.0 g (38.5%) of the desired compound, m.p. 70°–72° C.

B. A solution of 3.7 g (12.8 mmole) of the bromo compound obtained above and 50 ml tetrahydrofuran is cooled to −70° C. and 8.7 ml of 1.6M n-butyllithium in hexane is added dropwise at −65° C. The resulting mixture is stirred at −65° to −70° C. for 30 minutes. To this was added 1.5 ml (20 mmole) dimethylformamide at −65° C. and the cooling bath was removed. When the temperature of the mixture warmed to 10° C., 50 ml water and 50 ml ethyl ether was added and the mixture stirred. The ether layer was separated, washed with water, dried (MgSO₄) and the solvent evaporated in vacuo. The residual oil was triturated with hexane to yield 2.5 g (82%), m.p. 77°–80° C.

EXAMPLE 7

A. Employing the procedure of Part A of Example 6 with 1,2,3,4,4a,9b-hexahydrodibenzofuran* on an 0.08 molar scale gave 19.8 g crude material which was purified by silica gel chromatography, eluting with hexane to give 7.1 g (35%) of colorless crystals of the 6-bromo-derivative, m.p. 54°–56° C. Mass spectrum (m/e): 252 (M+), 254 (M +2).

Reaction of 7.0 g (27.6 mmole) of the above 6-bromo compound with n-butyllithium and dimethylformamide by the procedure of Example 6, Part B, gave 5.65 g (100%) of 6-bromo-1,2,3,4,4a,9b-hexahydrodibenzofuran as an oil. ¹H-NMR(CDCl₃) CHO singlet at delta 9.8.

B. Brominating 5.76 g (0.03 mole) 2-ethoxyethyl-2,3-dihydrobenzofuran by the method of Example 6, Part A, gave 7.8 g of crude product (oil) which afforded 2.7 g (33%) of 5-bromo-2-ethoxyethyl-2,3-dihydrobenzofuran upon silica gel chromatography, eluting with 10:1 hexane/ethyl acetate. ¹H-NMR(CDCl₃)ppm(delta): 6.5–6.65 (d, 2H), 7.1–7.4 (m, 2H).

This was reacted by the method of Example 6, Part B, to give 5-formyl-2-ethoxyethyl-2,3-dihydrobenzofuran as an oil in 91% yield. ¹H-NMR(CDCl₃)ppm(delta): 9.9 (s, 1H) CHO.

C. Bromination of thiachroman by the method of Compt. rend., 231, 1508-1510 (1950) afforded 6-bromothiachroman which was reacted by the method of Example 6, Part B, to afford 6-formylthiachroman in 98% yield.

*Prepared by hydrogenation of dibenzofuran over Raney nickel catalyst, in ethanol at 105 kg/cm², 80°-100° C. and purification by chromatography on a silica gel column. Mass spectrum (m/e): 174 (M+).

EXAMPLE 8

By reacting the appropriate starting bromo compound by the method of Example 6, Part B, afforded the following compounds in like manner.

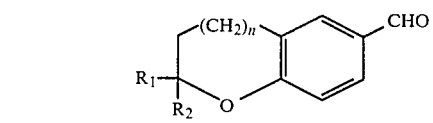

| n | R₁ | R₂ | (%) Yield | Physical Properties |
|---|---|---|---|---|
| 0 | C₆H₅ | H | 96 | oil, Mass Spectrum (m/e): 224 (M+). |
| 0 | —(CH₂)₅— | | 95 | oil, Mass Spectrum (m/e): 216 (M+). |
| 1 | C₆H₅CH₂ | H | 100 | oil. |
| 1 | C₆H₁₁ | H | 89 | oil, ¹H—NMR(CDCl₃)ppm (delta): 9.8 (s, 1H) CHO. |
| 1 | cyclohexyl-methyl | H | 100 | oil. |

EXAMPLE 9

6-Formyl-2-phenyl-3,4-dihydro-2H-benzopyran

A solution of 4.7 g (22 mmole) 2-phenyl-3,4-dihydro-2H-benzopyran* and 3.2 g (23 mmole) hexamethylenetetramine in 50 ml trifluoroacetic acid was heated at reflux (84°-88° C.) for 3.5 hours. The resulting mixture was concentrated in vacuo to a red oil, diluted with 125 ml water and stirred for 15 minutes. The mixture was made alkaline with saturated sodium carbonate solution, stirred for 10 minutes and filtered. The solid filter cake was extracted with ethyl ether, the extracts dried (MgSO₄) and solvent evaporated in vacuo to yield 1.6 g (30%) crude aldehyde as a gummy yellow solid. Purification by column chromatography on silica gel, eluting with 4:1 hexane/ethyl acetate, gave 391 mg of the pure aldehyde as a colorless solid (Rf 0.3 TLC). ¹H-NMR(CDCl₃)ppm(delta): 9.8 (s, 1H).

*This starting material was obtained by catalytic hydrogenation of commercial 2-phenyl-4-chromanone with Pd/C catalyst in acetic acid at 3.5 kg/cm², 50° C. for 5 hours. The crude product was purified by column chromatography on silica gel to obtain a 77% yield of product as white crystals.

EXAMPLE 10

A. dl-5-[(2-Benzyl-3,4-dihydro-2H-benzopyran-6-yl)methylene]thiazolidine-2,4-dione A mixture of 1.5 g (5.9 mmole) dl-2-benzyl-6-formyl-3,4-dihydro-2H-benzopyran, 1.2 g (14.8 mmole) anhydrous sodium acetate and 867 mg (7.4 mmole) 2,4-thiazolidinedione was heated in a oil bath at 140° C. while stirring. The mixture melted and started to resolidify within 5-10 minutes. Heating was continued for an additional 5-10 minutes and the resulting mixture was cooled to room temperature. Water, 50 ml, was added, the mixture stirred for 20 minutes and filtered. The yellow solid was air-dried overnight, triturated with acetone, 25 ml, filtered and washed with ethyl ether to yield 1.75 g (83%) of product as a yellow solid. TLC Rf 0.34 (2.5:1 v/v hexane/ethyl acetate); m.p. 183°-184° C.

Analysis calculated for $C_{20}H_{17}NO_3S$: C, 68.35; H, 4.88; N, 3.99%. Found: C, 67.93; H, 4.87; N, 3.87%.

B. Levorotatory isomer—Employing levorotatory-2-benzyl-6-formyl-3,4-dihydro-2H-benzopyran, $[\alpha]_D$-123.6°, provided in Example 25, as starting material in the above procedure affords (−)5-[(2-benzyl-3,4-dihydro-2H-benzopyran-6-yl)methylene]thiazolidine-2,4-dione in 100+percent crude yield as a yellow solid, m.p. 255° C.

C. Dextrorotatory isomer—Employing d-2-benzyl-6-formyl-3,4-dihydro-2H-benzopyran, $[\alpha]_D$+124.5°, provided in Example 24, as starting material, likewise affords the dextrorotatory isomer of the title compound, m.p. 257° C., M.S. 351 (M+) in 100+ percent crude yield as a yellow solid.

EXAMPLE 11

A. dl-5-[(2-Benzyl-3,4-dihydro-2H-benzopyran-6-yl)methyl]thiazolidine-2,4-dione and Sodium Salt To a solution of 1.75 g (5.0 mmole) dl-5-(2-benzyl-3,4-dihydro-2H-benzopyran-6-yl-methylene)-thiazolidine-2,4-dione in 225 ml glacial acetic acid was added 1.7 g 10% palladium-on-carbon catalyst (sulfur resistant) and the mixture was hydrogenated at 50 psi (3.5 bars), and room temperature overnight. The mixture was filtered, the filtrate concentrated in vacuo and the residue diluted with ethyl acetate. The resulting solution was washed with saturated sodium bicarbonate solution, brine and dried (MgSO4) Evaporation of solvent in vacuo gave the desired product as a colorless foam, 1.0 g (57%).

The above product was dissolved in 30 ml ethyl acetate, and 2.0 ml (2.8 mmole) sodium 2-ethylhexanoate added. The resulting mixture was stirred at room temperature overnight, the solvent evaporated in vacuo, the resulting colorless paste triturated with ethyl ether, filtered and washed with hexane to afford 840 mg (84%) of the desired sodium salt, m.p. 295°-300° C.

Mass spectrum (m/e): 353 (M+ +1), 237 (base peak).
$^1$H-NMR(DMSO-$d_6$)ppm(delta): 1.5-1.6 (m, 1H), 1.9 (m, 1H), 2.5 (dd, 1H), 2.6-2.7 (m, 2H), 2.9 (dd, 1H), 3.0 (dd, 1H), 3.3 (dd, 1H), 4.1 (dd, 1H), 4.1-4.2 (m, 1H), 6.6 (d, 1H), 6.9 (m, 2H), 7.2-7.3 (m, 5H).

Analysis calculated for $C_{20}H_{18}NO_3SNa$: C, 63.99; H, 4.83; N, 3.73%. Found: C, 63.75; H, 4.85; N, 3.61%.

B. Levorotatory isomer - Hydrogenation of (−)-5-[(2-benzyl-3,4-dihydro-2H-benzopyran-6-yl)methylene]thiazolidine-2,4-dione by the above method gave a 68% yield of the levorotatory isomer of the title compound after purification by silica gel column chromatography, $[\alpha]_D$−69.8° (20 mg/ml in methanol).

C. Dextrorotatory isomer—Hydrogenation of the (+)-isomer obtained in Example 10, Part C, likewise gave the corresponding dextrorotatory isomer in 65% yield after column chromatography, $[\alpha]_D$+64.5° (20 mg/ml in methanol).

EXAMPLE 12

In like manner employing the appropriate aldehyde (IV) in the procedure of Example 10 afforded the corresponding compound of formula (III)

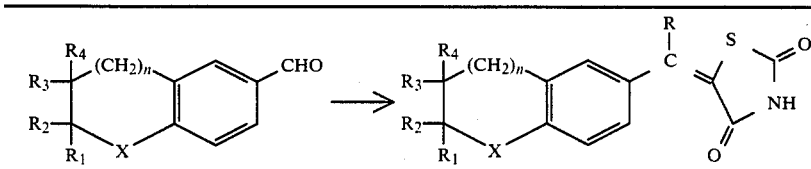

IV            III, R = H

| Oil bath temp., °C. | $R_1$ | $R_2$ | $R_3$ | $R_4$ | (%) Yield | Comment* |
|---|---|---|---|---|---|---|
| where X is O and n is zero: | | | | | | |
| 180 | $CH_3$ | H | H | H | 94 | 2 crops. |
| 200 | H | H | H | H | 69 | m.p. >265°; M.S. 247 (M+), 176, 163, 147, 131, 115. |
| 190 | n-butyl | H | H | H | 100+ (crude) | NMR 0.8-2.1 (m, 9H), 2.8-3.3 (m, 4H), 4.8 (m, 1H), 6.7-7.1 (m, 3H), 7.7 (s, 1H). |
| 155 | cyclohexyl | H | H | H | 88 | m.p. >300°; M.S. 329 (M+). |
| 150 | $C_6H_5$ | H | H | H | 62 | m.p. 290-292°; M.S. 323 (M+). |
| 180-200 | $C_6H_5CH_2$ | H | H | H | 79 | M.S. 337 (M+). |
| 150 | cyclohexylmethyl | H | H | H | 99 | m.p. 289-293° (dec.); M.S. 343 (M+), 272; I.R. 1693, 1598, 1589. |
| 150-155 | 4-$FC_6H_4CH_2$ | H | H | H | 97 | m.p. 279-283° (dec.); I.R. 1688, 1641, 1599, 1567. |
| 155 | 2-$FC_6H_4CH_2$ | H | H | H | 93 | m.p. 269-273° (dec.); M.S. 355 (M+), 284; I.R. 1693, 1593, 1571. |
| 155 | 1-methylcyclohexyl | H | H | H | 83 | m.p. >300°; M.S. 343 (M+); I.R. 1671, 1610, 1579. |
| 140 | 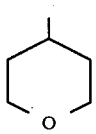 | H | H | H | 75 | yellow solid, m.p. 274-277°. |

-continued

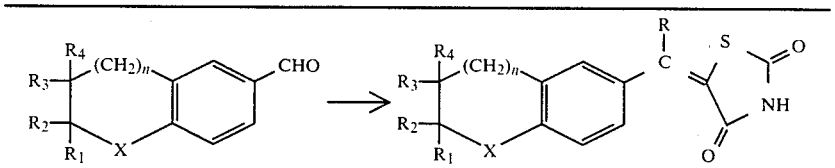

IV → III, R = H

| Oil bath temp., °C. | R₁ | R₂ | R₃ | R₄ | (%) Yield | Comment* |
|---|---|---|---|---|---|---|
| 180–200 | HOCH₂ | H | H | H | 90 | white solid, M.S. 277 (M+). |
| 185–190 | C₂H₅OCH₂CH₂ | H | H | H | 61 | solid, Rf 0.35 1:5 ethyl acetate/hexane + 5% acetic acid. |
| 190 | H | H | C₆H₅ | H | 50 | SG, hexane/ethyl acetate; M.S. 323 (M+), 252; NMR 4.2–5.0 (m, 3H), 6.7–7.3 (m + s, 8H), 7.5 (s, 1H). |
| 190 | H | H | C₆H₅CH₂ | H | 79 | TLC, Rf 0.2. |
| 180 | CH₃OCH₂ | H | H | H | 52 | solid, TLC, Rf 0.4. |
| 180–185 | —R₁ + R₃ = (CH₂)₄, R₂ = R₄ = H— | | | | 100+ crude | TLC, Rf 0.35; M.S. 301 (M+), NMR 1.1–2.2 (m, 8H), 3.2 (m, 1H), 4.7 (m, 1H), 6.7–7.6 (m, 4H). |
| 150 | —(CH₂)₅— | | H | H | 69 | yellow solid, m.p. 283–287° (dec.); M.S. 315 (M+). |
| where X is S and n is zero: | | | | | | |
| 190 | H | H | H | H | 63 | M.S. 263 (M+); NMR 3.3 (t, 4H), 5.3 (br. s, 2H), 7.3 (d, 4H). |
| 190 | CH₃ | H | H | H | 39 | yellow solid, NMR 1.4 (d, 3H), 3.0–4.2 (m, 3H), 7.3 (m, 3H), 7.7 (s, 1H). |
| 190–195 | C₆H₅CH₂ | H | H | H | 70 | yellow crystals, TLC Rf 0.35. |
| where X is O and n is 1: | | | | | | |
| 180 | H | H | H | H | 38 | m.p. >250°; M.S. 261 (M+) 190; NMR 1.9 (m, 2H), 2.7 (t, 2H), 4.1 (t, 2H), 6.7–7.4 (m, 3H), 7.5 (s, 1H). |
| 140 | C₆H₅ | H | H | H | 66 | yellow solid, TLC Rf 0.39; M.S. 337 (M+), 104; NMR 1.9–2.3 (m, 2H), 2.7–3.1 (m, 2H), 5.2 (dd, 1H), 6.9 (d, 1H), 7.2–7.5 (m, 8H). |
| 190–195 | cyclohexyl | H | H | H | 85 | yellow solid. |
| 140 | cyclohexylmethyl | H | H | H | 44 | yellow solid; M.S. 357 (M+), 55. |
| 140 | H | H | —(CH₂)₅— | | 85 | yellow solid; m.p. 310–314°; M.S. 329 (M+), 43. |
| 180° | 2-CH₃OC₆H₄CH₂ | H | H | H | — | m.p. 100–110° (dec.). |
| 180° | 3-CH₃OC₆H₄CH₂ | H | H | H | — | m.p. 210–215° (dec.). |
| 180° | 4-CH₃OC₆H₄CH₂ | H | H | H | — | m.p. 227–229° (dec.). |
| where X is O and n is 2: | | | | | | |
| 180 | H | H | H | H | 50 | m.p. >250°; TLC, Rf 0.5. |

*I.R.: infrared spectrum (KBr) cm⁻¹.
m.p.: melting point, °C.
M.S.: mass spectrum (m/e); (M+), molecular ion.
NMR: ¹H—NMR(CDCl₃)ppm(delta).
S.G.: purified by column chromatography on silica gel.
TLC: thin-layer chromatography.

EXAMPLE 13

By hydrogenation of the appropriate methylene compound of formula (III) obtained in the previous Example, the corresponding saturated compound of formula (II) or its sodium salt is obtained by the procedure of Example 11.

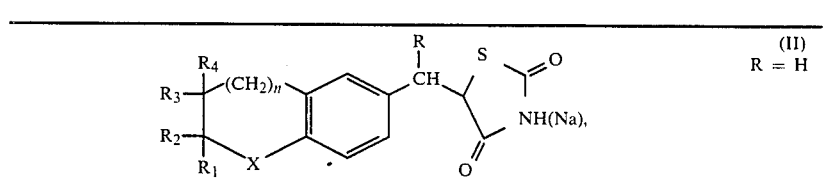

| R₁ | R₂ | R₃ | R₄ | (%) Yield | Comment |
|---|---|---|---|---|---|
| where X is O and n is zero: | | | | | |
| CH₃ | H | H | H | 43 | m.p. 165–166° from ethyl ether; M.S. 263 (M+). |

-continued

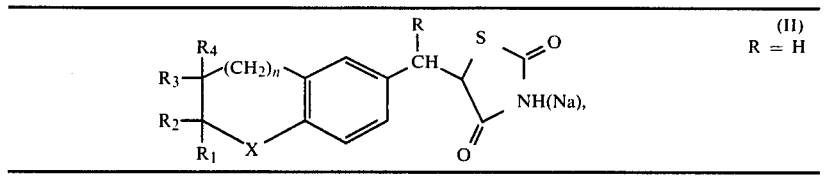

(II) R = H

| R1 | R2 | R3 | R4 | % | Notes |
|---|---|---|---|---|---|
| H | H | H | H | | m.p. 162-164°, S.G.[a] |
| n-butyl | H | H | H | | M.S. 305 (M+), 189, 121; NMR 0.8-2.1 (m, 9H), [2.8(q), 3.0(q), 3.3(m), 4H], 4.75 (m, 1H), 4.85 (q, 1H), 6.7 (d, 1H), 6.9 (d, 1H), 7.1 (s, 1H).[i] |
| cyclohexyl | H | H | H | 65 | I.R. 1758, 1696; M.S. 331 (M+); Na salt m.p. >300°. |
| $C_6H_5$ | H | H | H | 42 | m.p. 143-147°; M.S. 325 (M+); I.R. 1758, 1673. |
| $C_6H_5CH_2$ | H | H | H | 29 | S.G.; m.p. 130-136° (from ether/hexane); M.S. 339 (M+), 223[b]; Na salt, m.p. >290°. |
| cyclohexyl-methyl | H | H | H | 67 | m.p. 165-172°; M.S. 345 (M+); Na salt m.p. 284° (dec.)[c] |
| $4\text{-}FC_6H_4CH_2$ | H | H | H | 65 | M.S. 357 (M+), 241; NMR 2.8-3.6 (m, 6H), 4.4 (dd, 1H), 4.9 (m, 1H), 6.5-7.2 (m, 7H), 9.0 (bs, 1H). |
| $2\text{-}FC_6H_4CH_2$ | H | H | H | 67 | Foam; M.S. 357 (M+); I.R. 1756, 1694, 1490; Na salt m.p. 288-292° (dec.). |
| 1-methyl-cyclohexyl | H | H | H | 89 | yellow foam, M.S. 345 (M+), 229; I.R. 1757, 1694; Na salt m.p. 291-293° (dec.). |
| (tetrahydropyran-4-yl) | H | H | H | 70 | yellow solid; Na salt m.p. 310-312° (dec.). |
| $HOCH_2$ | H | H | H | 20 | S.G.; m.p. 137-142°; M.S. 279 (M+), 163.[d] |
| $C_2H_5OCH_2CH_2$ | H | H | H | 52 | m.p. 93-100°; M.S. 321 (M+), 205.[e] |
| H | H | $C_6H_5$ | H | 31 | hydrogenated in 1:1 acetic acid/tetrahydrofuran as solvent; m.p. 68-74°.[h] |
| H | H | $C_6H_5CH_2$ | H | 5 | same solvent as above; M.S. 339 (M+), 223, 133; S.G.; Na salt m.p. 198° (dec.). |
| $CH_3OCH_2$ | H | H | H | 55 | M.S. 294 (M+ + 1), 177; NMR 2.8-3.8 (m, 9H), 4.4 (dd, 1H), 4.9 (m, 1H), 6.6-7.0 (m, 3H). |
| —R1 + R3 = (CH2)4, R2 = R4 = H— | | | | 61 | oil, M.S. 303 (M+); S.G.[f] |
| —(CH2)5— | | H | H | 55 | S.G.; m.p. 157-160°; M.S. 317 (M+), I.R. 1761, 1672.[g] | where X is O and n is 1:

| R1 | R2 | R3 | R4 | % | Notes |
|---|---|---|---|---|---|
| H | H | H | H | 40 | S.G.; m.p. 167-168° from ethyl acetate/hexane; M.S. 263 (M+), 147; NMR 1.3-1.7 (m, 2H), 2.3 (t, 2H), 2.8 (m, 2H), 3.6 (t, 2H), 4.2 (m, 1H), 6.1-6.6 (m, 3H). |
| $C_6H_5$ | H | H | H | 56 | m.p. 131-134°.[j] |
| cyclohexyl | H | H | H | 34 | m.p. 155-157°; M.S. 345 (M+), 229; Na salt.[k] |
| cyclohexyl-methyl | H | H | H | 88 | m.p. 107-112° (from $CH_2Cl_2$/hexane); M.S. 359 (M+), 243; Na salt m.p. 300-305° (dec.). |
| H | H | —(CH2)5— | | 49 | m.p. 122-124°; M.S. 331 (M+), 215; I.R. 1680. |
| $2\text{-}CH_3OC_6H_4CH_2$ | H | H | H | 81 | Na salt, m.p. 250-260° (dec.). |
| $2\text{-}HOC_6H_4CH_2$** | H | H | H | 81 | Na salt, m.p. 230° (dec.). |
| $3\text{-}CH_3OC_6H_4CH_2$ | H | H | H | 62 | Na salt, m.p. 260° (dec.). |
| $3\text{-}HOC_6H_4CH_2$** | H | H | H | 62 | Na salt, m.p. 220-240° (dec.). |
| $4\text{-}CH_3OC_6H_4CH_2$ | H | H | H | 83 | Na salt, m.p. 245-255° (dec.). |
| $4\text{-}HOC_6H_4CH_2$** | H | H | H | 83 | Na salt, m.p. 260-265° (dec.). | where X is O and n is 2:

| R1 | R2 | R3 | R4 | % | Notes |
|---|---|---|---|---|---|
| H | H | H | H | 49 | S.G.; m.p. 176-177°; M.S. 277 (M+). |

*H.P.C.: purified by high pressure chromatography on silica gel.
I.R.: infrared spectrum (KBr) cm$^{-1}$.
m.p.: melting point, °C.
M.S.: mass spectrum (m/e); (M+), molecular ion.
S.G.: purified by silica gel column chromatography.

-continued

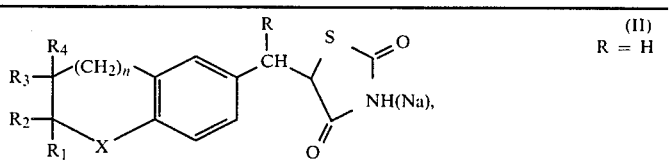

**The hydroxy substituted benzyl compounds were obtained from the corresponding methoxybenzyl analogs by refluxing in 48% hydrogen bromide in glacial acetic acid for about two hours, evaporation to dryness in vacuo, partitioning the residue between ethyl acetate and saturated sodium bicarbonate solution, washing the organic phase with water, brine, evaporation to dryness and carbon treating a methanol solution of the residue. The methanol filtrate was then converted to sodium salt with one equivalent of sodium methoxide.

| | |
|---|---|
| [a] Analysis calculated for $C_{12}H_{11}O_3NS$: | C, 57.83; H, 4.45; N, 5.62%. |
| Found: | C, 57.71; H, 4.69; N, 5.60%. |
| [b] Analysis calculated for $C_{19}H_{17}O_3NS$: | C, 67.25; H, 5.05; N, 4.13%. |
| Found; | C, 67.21; H, 5.07; N, 4.03%. |
| [c] Analysis calculated for $C_{19}H_{23}O_3NSNa.0.5H_2O$: | C, 60.61; H, 6.16; N, 3.72%. |
| Found: | C, 61.03; H, 6.48; N, 3.27%. |
| [d] Analysis calculated for $C_{13}H_{13}O_4NS$: | C, 55.91; H, 4.70; N, 5.02%. |
| Found: | C, 55.73; H, 4.79; N, 4.78%. |
| [e] Analysis calculated for $C_{16}H_{19}O_4NS$: | C, 59.80; H, 5.96; N, 4.36%. |
| Found: | C, 59.65; H, 6.07; N, 4.35%. |
| [f] Analysis calculated for $C_{16}H_{17}O_3NS.0.25H_2O$: | C, 62.43; H, 5.73; N, 4.55%. |
| Found: | C, 62.31; H, 5.63; N, 4.35%. |
| [g] Analysis calculated for $C_{17}H_{19}O_3NS$: | C, 64.33; H, 6.03; N, 4.41%. |
| Found: | C, 63.96; H, 6.07; N, 4.24%. |
| [h] Analysis calculated for $C_{18}H_{15}O_3NS$: | C, 66.44; H, 4.65; N, 4.31%. |
| Found: | C, 66.73; H, 4.78; N, 4.08%. |
| [i] Analysis calculated for $C_{16}H_{19}NO_3S$: | C, 62.92; H, 6.28; N, 4.59%. |
| Found: | C, 62.46; H, 6.15; N, 4.47%. |
| [j] Analysis calculated for $C_{19}H_{17}O_3NS$: | C, 67.24; H, 5.05; N, 4.13%. |
| Found: | C, 67.08; H, 5.08; N, 4.11%. |
| [k] Analysis calculated for $C_{19}H_{23}O_3NS$: | C, 66.05; H, 6.72; N, 4.06%. |
| Found: | C, 66.23; H, 6.64; N, 4.00%. |

EXAMPLE 14

Sodium 5-[(2,2-Dimethyl-3-phenyl-3,4-dihydro-2H-benzopyran-6-yl)methyl]thiazolidine-2,4-dione, (II, R=R$_4$=H, R$_1$=R$_2$=CH$_3$ R$_3$=C$_6$H$_5$, X=O, n=1)

A. 6-Formyl-2,2-dimethyl-3-phenyl-3,4-dihydro-2H-benzopyran (IV, R=R$_4$=H, R$_1$=R$_2$=CH$_3$, R$_3$=C$_6$H$_5$, X=O, n=1)

Under anhydrous conditions and in a nitrogen atmosphere, to a solution of 4.6 g (20 mmole) 2-(1,1-dimethylbenzyl)-2,3-dihydrobenzofuran in 75 ml methylene dichloride at 0° C. was added 7.6 g (4.4 ml, 40 mmole) titanium tetrachloride in one portion. To the resulting mixture was added dropwise 2.5 g (2.0 ml, 22 mmole) 1,1-dichloromethylmethyl ether and stirring continued at 0° C. for 45 minutes. Thin-layer chromatography of a sample of the reaction mixture (hexane/ethyl ether, 12:1) showed no starting material (Rf 0.62), but two products at Rf 0.14 and 0.25. The reaction mixture was poured into 100 ml water, stirred for ten minutes and extracted with ethyl acetate (3×125 ml). The combined extracts were washed twice with brine, dried (MgSO$_4$) and the solvent evaporated to afford 5.3 g of amber, viscous oil. The oil was flash chromatographed on a silica gel column (0.6 cm diameter, 17 cm long) eluting with 10:1 hexane/ethyl ether to obtain 1.7 g of the less polar product (8-formyl isomer), m.p. 88°-92° C., and 2.1 g of the desired less polar product, (6-formyl isomer) as a light yellow oil. $^1$H-NMR(CDCl$_3$)ppm(delta): 1.3 (d, 6H), 2.95-3.1 (m, 2H), 3.2-3.3 (q, 1H), 6.95 (d, 1H), 7.2-7.4 (m, 5H), 7.7 (d, 2H), 9.85 (s, 1H). M.S. (m/e): 266 (parent), 131 (base).

B. 5-[(2,2-Dimethyl-3-phenyl-3,4-dihydro-2H-benzopyran-6-yl)methylene]-thiazolidine-2,4-dione (III, R=R$_4$=H, R$_1$=R$_2$=CH$_3$, R$_3$=C$_6$H$_5$, X=O, n=1)

A mixture of 1.7 g (6.4 mmole) 6-formyl-2,2-dimethyl-3-phenyl-3,4-dihydro-2H-benzopyran, 1.4 g (16.5 mmole) anhydrous sodium acetate and 970 mg (8.3 mmole) 2,4-thiazolidinedione was heated with stirring in an oil bath at 140° C. for 35 minutes. The reaction mixture was cooled, 50 ml water added, the mixture stirred at room temperature for 16 hours. The yellow solid was collected by filtration, air dried and triturated with acetone (50 ml) for 30 minutes. Filtration and washing the collected solids with ethyl ether and air drying afforded the desired product as a yellow solid, 910 mg (40%), m.p. 231°-235° C. Reworking the mother liquor gave an additional 400 mg of product. M.S. (m/e): 365 (parent), 131 (base).

C. 5-[(2,2-Dimethyl-3-phenyl-3,4-dihydro-2H-benzopyran-6-yl)methyl]thiazolidine-2,4-dione Upon hydrogenation of a mixture of 1.5 g (4.1 mmole) of the product obtained in Part B, above, 1.5 g of 10% palladium-on-carbon catalyst and 230 ml glacial acetic acid at 3.5 bars, 25° C. for 18 hours, removal of the catalyst by filtration through diatomaceous earth and evaporation of acetic acid, a crude oil was obtained. The oil was taken up in 200 ml ethyl acetate, washed with sodium bicarbonate solution (3 times), brine (3 times), dried (MgSO$_4$) and the solvent evaporated in vacuo to give 1.2 g (80%) of the desired product, m.p. 53°-68° C. M.S. (m/e): 367 (parent), 131 (base).

D. To a solution of 1.14 g (3.1 mmole) of the above product in 35 ml ethyl acetate was added 2.23 l (3.1 mmole), 1.391 molar sodium 2-ethylhexanoate and the mixture was stirred at room temperature for 50 hours. The mixture was concentrated in vacuo to a white paste, triturated with 3:1 hexane/ethyl acetate and filtered. The white solid cake was triturated with hexane alone, and filtered to yield 730 mg (60%) of the title sodium salt, m.p. 195°–210° C. $^1$H-NMR($D_2O$)ppm-(delta): 1.2 (d, 6H), 2.5 (m, 2H), 2.85 (d, 1H), 3.0–3.2 (m, 2H), 3.3–3.4 (d, 2H), 4.1–4.2 (m, 1H), 6.7 (d, 1H), 6.9–7.0 (d, 2H), 7.2–7.4 (s, 5H).

EXAMPLE 15

5-[(2-Benzyl-2,3-dihydrobenzothiophene-5-yl)methyl]-thiazolidine-2,4-dione (II, R=$R_2$=$R_3$=$R_4$=H, X=S, n=zero)

To a solution of 2.0 g (5.6 mmole)5-](2-benzyl-2,3-dihydrobenzothiophene-5-yl-methylene]thiazolidine-2,4-dione, provided in Example 12, in 75 ml refluxing glacial acetic acid was added 10 g zinc dust in small portions over a 15 minute period. The mixture was then cooled, filtered and the filtrate evaporated to dryness in vacuo to provide a residual oil. The oil was purified by column chromatography on silica gel, eluting with 4:1 hexane/ethyl acetate. The combined product fractions were evaporated to dryness, the residual oil triturated with hexane to obtain 212 mg (10%) of crystals, m.p. 90°–94° C. Mass spectrum (m/e): 355 (M+), 264, 239.

Analysis calculated as $C_{19}H_{17}O_2NS_2$: C, 64.22; H, 4.82; N, 3.94%. Found: C, 63.99; H, 4.96; N, 3.73%.

A portion of the above product (98 mg, 0.28 mmole) in 10 ml ethyl acetate was treated with a equimolar amount of sodium 2-ethylhexanoate (1.39M). After standing at room temperature for 1.5 hours, the mixture was concentrated to dryness, the residue triturated with 10 ml warm hexane, cooled and filtered to obtain 90 mg of sodium salt as a white solid.

EXAMPLE 16

5-[(2-Benzyl-2,3-dihydro-1,1-dioxobenzothiophene-5-yl)methyl]thiazolidine-2,4-dione and Its Sodium Salt To a solution of 330 mg (0.92 mmole) 5-](2-benzyl-2,3-dihydrobenzothiophene-5-yl)methyl]thiazolidine-2,4dione in 20 ml glacial acetic acid was added 51 ml (50 mmole) 30% hydrogen peroxide and the mixture stirred at room temperature for 20 hours.* The mixture was poured into 50 ml water, stirred for two hours, filtered and the precipitated solid dried at 80° C. to afford 146 mg of product, m.p. 100°–130° C. which gave a single spot upon thin-layer chromatography ($SiO_2$), employing ethyl acetate (1 part), hexane (2 parts) and acetic acid (5%) as solvent. Mass spectrum (m/e): 387 (M+).

Analysis calculated for $C_{19}H_{17}O_4NS_2$: C, 58.91; H, 4.42; N, 3.62%. Found: C, 58.61; H, 4.73; N, 3.39%.

The above sulfone (121 mg) was converted to sodium salt by reaction with sodium 2-ethylhexanoate in quantitative yield.

*When the reaction was carried out for shorter periods (e.g. six hours), the product was found to be a mixture of sulfoxide (Rf 0.2) and the desired sulfone (Rf 0.3).

EXAMPLE 17

A. Reaction of 1.6 g (5.77 mmole) of 5-[(2-methyl-2,3-dihydrobenzothiophene-5-yl)xethylene]thiazolidine-2,4-dione, provided in Example 12, in 50 ml acetic acid with 3.77 g (57.7 mmole) zinc dust by the procedure of Example 15 afforded 5-[(2-methyl-2,3-dihydrobenzothiophene-5-yl)methyl]thiazolidine-2,4-dione, 200 mg, as an oil which was crystallized from ethyl ether, m.p. 137°–139° C. Mass spectrum (m/e): 279 (M+), 163.

Analysis calculated for $C_{13}H_{13}NO_2S_2$: C, 55.88; H, 4.69; N, 5.01%. Found: C, 55.73; H, 4.65; N, 4.84%.

B. Oxidation of 75 mg of the product of Part A with hydrogen peroxide in acetic acid by the method of Example 16 gave 20 mg of the corresponding sulfone, 5-[(2-methyl-2,3-dihydro-1,1-dioxobenzothiophenyl-5-yl)methyl]thiazolidine-2,4-dione, Mass spectrum (m/e): 311 (M+).

The sodium salt was prepared by reaction of the above product with an equimolar amount of sodium 2-ethylhexanoate in ethyl acetate, stirring the resulting mixture for one hour, evaporation of solvent in vacuo and trituration of the residue with warm hexane. The sodium salt was obtained in 88% yield as a colorless solid, soluble in water and dimethylsulfoxide.

EXAMPLE 18

5-[(2,3-Dihydrobenzothiophene-5-yl)methyl]-thiazolidine-2,4-dione and Its Sulfoxide A. Reduction of 5-[(2,3-dihydrobenzothiophene-5-yl)methylene]thiazolidine-2,4-dione, provided in Example 12, on a 2.24 mmolar scale, by the method of Example 15, affords the title dihydrobenzothiophene compound as a yellow oil which was purified by column chromatography on silica gel, eluting with 2:1 hexane/ethyl acetate, m.p. 167°–169° C. $^1$H-NMR($CDCl_3$)ppm(delta): 3.0 (d), 3.2 (m, obscured by $H_{20}$), 4.9 (q), 7.0 (d), 7.5 (m). Analysis calculated for $C_{12}H_{11}NO_2S_2.0.25H_2O$: C, 53.41; H, 4.29; N, 5.19%. Found: C, 53.72; H, 4.19; N, 5.03%.

B. To a solution of 260 mg (1.0 mmole) of the product obtained in Part A, above, in 20 ml acetic acid (warmed to dissolve, then cooled to room temperature) was added 1 ml (10 mmole) 30% hydrogen peroxide and the mixture was stirred at room temperature for 15 minutes. The reaction was quenched by addition of ice and solid sodium bicarbonate until starch paper showed negative (peroxide test). The resulting mixture was concentrated to dryness in vacuo, the solid residue stirred with 25 ml water for 30 minutes and the white solid collected by filtration and dried at 80° C., 0.1 mm pressure, to afford 224 mg of product which was identified as the 1-oxide (sulfoxide), m.p. 228°–231° C. (dec.). Mass spectrum (m/e): 281 (M+), 165 (100%).

EXAMPLE 19

1-(2-Benzyl-3,4-dihydro-2H-benzopyran-6-yl)-1-(thiazolidine-2,4-dione-5-yl)ethane By reaction of 6-acetyl-2-benzyl-3,4-dihydro-2H-benzopyran with 2,4-thiazolidinedione by the method of Example 10 affords the corresponding olefin of formula

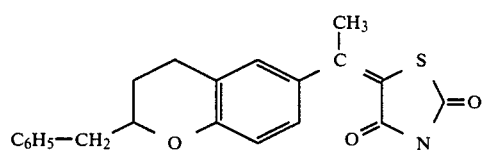

which is reduced to the title compound by the method of Example 11.

In like manner the corresponding olefins of formula (III) are obtained from the appropriate starting aldehyde or ketone by the method of Example 10 at a temperature of from 100° to 250° C. The olefins are, in turn, reduced by the method of Example 11 to provide the corresponding compound of formula (II), below.

Structure (II):

$$\text{R}_3\text{-}\underset{\text{R}_1}{\overset{\text{R}_4}{\text{C}}}(\text{CH}_2)_n\text{-C}_6\text{H}_3\text{-CHR-CH}\begin{pmatrix}\text{S}\\\text{N}\end{pmatrix}\text{C=O}$$

(with R_2 on ring, X in ring)

| n | X | R | R₁ | R₂ | R₃ | R₄ |
|---|---|---|---|---|---|---|
| 0 | O | CH₃ | H | H | H | H |
| 0 | O | CH₃ | cyclopentyl | H | H | H |
| 1 | O | CH₃ | cyclohexyl | H | H | H |
| 1 | O | C₂H₅ | cycloheptyl | H | H | H |
| 0 | O | C₂H₅ | 3-methyl-cyclopentyl | H | H | H |
| 0 | O | CH₃ | 1-methyl-cyclohexyl | H | H | H |
| 2 | O | CH₃ | 1-methyl-cycloheptyl | H | H | H |
| 0 | O | CH₃ | 2-pyridyl | H | H | H |
| 1 | O | H | 4-pyridyl | H | H | H |
| 1 | O | H | 3-thienyl | H | H | H |
| 1 | O | H | 2-furyl | H | H | H |
| 1 | S | H | 1-naphthyl | H | H | H |
| 1 | O | H | p-biphenylyl | H | H | H |
| 1 | S | H | tetrahydrofuran-2-yl | H | H | H |
| 1 | O | CH₃ | 2-thienyl | H | H | H |
| 1 | S | CH₃ | 3-furyl | H | H | H |
| 0 | O | CH₃ | 2-napthyl | H | H | H |
| 0 | S | CH₃ | p-biphenylyl | H | H | H |
| 0 | O | CH₃ | tetrahydrofuran-4-yl | H | H | H |
| 0 | S | CH₃ | tetrahydrothien-2-yl | H | H | H |
| 0 | O | C₂H₅ | tetrahydropyran-4-yl | H | CH₃ | H |
| 0 | S | C₂H₅ | C₆H₅ | CH₃ | C₆H₅ | H |
| 0 | O | C₂H₅ | 4-FC₆H₄ | H | H | H |
| 0 | S | C₂H₅ | 3-ClC₆H₄ | CH₃ | n-C₄H₉ | H |
| 1 | S | C₂H₅ | 3-CH₃C₆H₄ | H | C₂H₅ | H |
| 1 | S | C₂H₅ | 4-(CH₃)₃CC₆H₄ | H | (CH₃)₂CH | H |
| 1 | O | C₂H₅ | 4-(CH₃)₂CHC₆H₄ | H | n-C₆H₁₃ | H |
| 1 | S | C₂H₅ | 2-C₂H₅OC₆H₄ | H | C₆H₅ | H |
| 2 | O | H | 2-ClC₆H₄ | H | 4-FC₆H₄ | H |
| 1 | S | H | 4-BrC₆H₄ | CH₃ | H | H |
| 1 | O | H | 2-FC₆H₄ | H | C₆H₅CH₂ | H |
| 1 | S | H | 3-C₂H₅C₆H₄ | H | C₆H₅CH₂ | H |
| 1 | O | H | 4-CH₃OC₆H₄ | H | 4-BrC₆H₄ | H |
| 2 | S | H | 4-n-C₄H₉OC₆H₄ | H | 4-CH₃C₆H₄ | H |
| 1 | O | H | 2-CH₃SC₆H₄ | H | H | H |
| 0 | S | H | 4-(CH₃)₂CH—SC₆H₅ | H | H | H |
| 0 | O | CH₃ | t-(CH₃)₃C—SC₆H₅ | H | H | H |
| 1 | O | CH₃ | CH₃ | H | H | H |
| 1 | O | CH₃ | (CH₂)₃CH₃ | H | H | H |
| 1 | O | CH₃ | (CH₂)₅CH₃ | H | H | H |
| 1 | O | CH₃ | CH₂CH₂OH | H | H | H |
| 1 | O | CH₃ | CH₂OH | H | H | H |
| 1 | O | CH₃ | CH₂CH(OH)CH₃ | H | H | H |
| 1 | S | CH₃ | CH₂CH(OH)(CH₂)₃CH₃ | H | H | H |
| 1 | O | C₂H₅ | CH₂O—i-C₄H₉ | H | H | H |
| 2 | S | H | CH₂CH₂OCH₃ | H | H | H |
| 0 | S | H | (CH₂)₃O—n-C₃H₇ | H | H | H |
| 0 | S | H | (CH₂)₅OCH₃ | H | H | H |
| 0 | S | CH₃ | (CH₂)₆O—n-C₄H₉ | H | H | H |
| 0 | S | H | CH₂SCH₃ | H | H | H |
| 0 | S | H | (CH₂)₂SCH₂CH₃ | H | H | H |
| 0 | O | H | CH(CH₃)OCH₃ | H | H | H |
| 0 | O | C₂H₅ | CH(CH₃)S(CH₂)₃CH₃ | H | H | H |
| 0 | O | H | C(CH₃)₂OC₂H₅ | H | H | H |
| 0 | O | H | C(CH₃)₂OCH₃ | H | H | H |
| 0 | O | H | C(CH₃)₂—2-furyl | H | H | H |
| 1 | O | CH₃ | CH₂—3-furyl | H | H | H |
| 1 | O | H | CH₂—2-pyridyl | H | H | H |
| 1 | O | H | (CH₂)₂—4-pyridyl | H | H | H |
| 1 | O | H | (CH₂)₃—2-thienyl | H | H | H |
| 1 | O | C₂H₅ | (CH₂)₅—(tetrahydrofuran-2-yl, O ring) | H | H | H |
| 1 | O | H | CH₂—(tetrahydrothien-2-yl, S ring) | H | H | H |
| 1 | O | H | CH₂—1-naphthyl | H | H | H |
| 1 | O | H | (CH₂)₃—2-naphthyl | H | H | H |
| 0 | O | H | C(CH₃)₂—1-naphthyl | H | H | H |
| 0 | O | H | (CH₂)₆—1-naphthyl | H | H | H |
| 0 | O | H | CH₂—cyclopentyl | H | H | H |
| 0 | S | H | (CH₂)₃—cyclohexyl | H | CH₃ | H |
| 0 | O | H | (CH₂)₅—cyclopentyl | H | H | H |
| 0 | S | H | CH₂—cycloheptyl | H | H | H |
| 1 | O | H | (CH₂)₆—cyclohexyl | H | H | H |
| 0 | O | H | CH₂—4-Cl—C₆H₄ | H | (CH₃)₂CH | H |
| 1 | O | H | (CH₂)₂—2-FC₆H₄ | H | H | H |
| 0 | O | H | (CH₂)₃—4-BrC₆H₄ | H | H | H |
| 1 | S | H | (CH₂)₄—3-CH₃OC₆H₄ | H | CH₂C₆H₅ | H |
| 0 | O | H | (CH₂)₅—2-CH₃C₆H₄ | H | H | H |
| 1 | O | CH₃ | (CH₂)₆—4-n-C₄H₉C₆H₄ | H | H | H |
| 0 | O | H | CH(CH₃)C₆H₅ | H | 4-FC₆H₄ | H |
| 1 | O | H | CH(CH₃)—4-CH₃SC₆H₄ | H | H | H |
| 0 | S | H | —(CH₂)₄— | | H | H |
| 1 | O | H | —(CH₂)₅— | | H | H |
| 0 | O | H | —(CH₂)₆— | | H | H |
| 1 | O | H | H | H | —(CH₂)₄— | |
| 0 | O | H | H | H | —(CH₂)₆— | |
| 1 | O | H | H | H | —(CH₂)₅— | |
| 0 | O | H | H | H | —(CH₂)₄— | |
| 0 | O | CH₃ | H | | —(CH₂)₃— | H |
| 1 | O | C₂H₅ | H | | —(CH₃)₄— | H |
| 1 | O | H | H | | —(CH₂)₃— | H |
| 0 | O | H | H | | —(CH₂)₄— | H |
| 1 | O | H | (CH₂)₃C₆H₅ | H | H | H |
| 0 | O | H | CH₃ | CH₃ | 4-BrC₆H₄ | H |

EXAMPLE 20

6-Formyl-1,1-dioxothiachroman

A solution of 10.3 g (57.8 mmole) 6-formylthiachroman in 300 ml methylene chloride was cooled to −10° C. and 25.8 g (127.2 mmole) 85% 3-chloroperbenzoic acid was added in portions while maintaining the temperature of the mixture below −5° C. The mixture was stirred while warming to room temperature and allowed to stir overnight. The solids were removed by filtration, the filtrate diluted with methylene chloride, washed with water, sodium bicarbonate, water again, brine and dried (MgSO₄). Evaporation of solvent afforded 6.04 g (50%) of the desired sulfone, m.p. 185°–187° C. M.S. (m/e): 210 (M+).

EXAMPLE 21

2-Benzyl-6-formyl-1,1-dioxothiachroman

A. 6-(1,3-Dioxolan-2-yl)-1,1-dioxothiachroman

To a mixture of 3.0 g (14.3 mmole) 6-formyl-1,1dioxothiachroman and 140 ml toluene was added 15.9 ml ethylene glycol and 0.66 g (3.5 mmole) p-toluenesulfonic acid hydrate. The mixture was heated at reflux for 18 hours or until no further water was collected in the attached water separator (Dean-Stark trap). The reaction mixture was cooled, diluted with ethyl acetate, washed with water, sodium bicarbonate, water again, brine and dried (MgSO$_4$). Evaporation of solvent in vacuo gave 3.73 g of residual oil which solidified on standing. Mass spectrum (m/e): 254 (M+).

B. A solution of 254 mg (1.0 mmole) 6-(1,3-dioxolan-2-yl)-1,1-dioxothiachroman in 10 ml tetrahydrofuran was cooled to 0° C. and 1.15 mmole of 2.3M n-butyllithium was added dropwise. The resulting red solution was stirred for 30 minutes at 0° C., 137 microliters (1.15 mmole) benzyl bromide was added and stirring continued at 0° C. for one hour, then at room temperature for two hours. The reaction was quenched by addition of citric acid. The mixture was taken up in ethyl ether, washed with brine, dried (MgSO$_4$) and the solvents evaporated. The residue was taken up in 15 ml tetrahydrofuran, 10 ml 3.5% aqueous perchloric acid added and the mixture stirred overnight. Extraction with ethyl ether, washing with brine, drying (MgSO$_4$) and evaporation of solvent gave the title compound as an oil, Rf 0.6 on silica gel TLC (9:1 methylene chloride/ethyl ether).

EXAMPLE 22 dl-2-Benzylchroman-6-carboxylic Acid

To a flask containing 600 ml dry tetrahydrofuran (THF) was added 108 ml (165 mmole) 1.6M n-butyllithium in hexane and the mixture cooled to −70° C. A solution of 25 g (82.5 mmole) 2-benzyl-6-bromochroman in 200 ml dry THF was added dropwise over ten minutes. Cooling was then removed and carbon dioxide gas was bubbled through the mixture for 15 minutes. The mixture was poured into 1200 ml cold water containing 60 ml 6N hydrochloric acid. The resulting mixture was extracted with ethyl acetate, the extracts dried (Na$_2$SO$_4$) and solvent evaporated to afford the desired carboxylic acid, 17.3 g (78% yield), m.p. 177°–179° C.

EXAMPLE 23

Resolution of dl-2-Benzylchroman-6-carboxylic Acid

A. A solution of 25.0 g (93 mmole) dl-2-benzylchroman-6-carboxylic acid in 800 ml methanol was heated to boiling, cooled to 40° C. and 12.4 g (102 mmole) R(+)-alpha-methylbenzylamine was added. No precipitate formed on standing. The methanol was evaporated in vacuo and the solid residue triturated with 200 ml hexane and insolubles removed by filtration to afford 36 g of white solid, m.p. 172°–175° C. $[\alpha]_D^{23}+52.3°$ (20 mg/ml, methanol).

Evaporation of the mother liquor in vacuo gave 9.5 g solid, m.p. 141°–150° C. $[\alpha]_D^{23}-24.6°$ (19.9 mg/ml, methanol).

The dextrorotatory isomer above (36 g) was combined with like fractions from other runs to give 50.9 g. This was recrystallized from 3200 ml ethyl acetate and, after allowing the solution to stand at room temperature for 1.5 hours, the precipitated white solid was collected by filtration to give 29.4 g, m.p. 176°–178° C., $[\alpha]_D^{23}+69.3°$. Two more crystallizations in the same manner gave 17.3 g of pure isomer, m.p. 179°–180° C., $[\alpha]_D^{23}+84.66°$ (20.5 mg/ml, methanol).

B. Repeating the above procedure but with S(−)-alphamethylbenzylamine gave the levorotatory salt 8.6 g, $[\alpha]_D^{23}-88.6°$ (20 mg/ml, methanol).

Analysis calculated for C$_{25}$H$_{27}$NO$_3$: C, 77.09; H, 6.99; N, 3.60%. Found: C, 76.92; H, 6.96; N, 3.52%.

C. A slurry of 5.0 g (13 mmole) of the dextrorotatory salt, $[\alpha]_D^{23}+86.66°$, was slurried in water, 200 ml, and 150 ml ethyl acetate added. The mixture was stirred while adding 6N hydrochloric acid to pH ~2. The mixture was stirred for a few more minutes and the layers separated. The aqueous phase was extracted with 100 ml ethyl acetate. The organic layers were combined, washed with brine, dried (Na$_2$SO$_4$) and the solvent evaporated in vacuo to yield 3.3 g (94%) d-2-benzylchroman-6-carboxylic acid, $[\alpha]_D^{23}+113.70°$ (20 mg/ml, acetone)

D. In the same manner 2.0 g (5.12 mmole) of the levorotatory salt, $[\alpha]_D^{23}-88.66°$, gave 1.37 g l-2-benzylchroman-6-carboxylic acid, $[\alpha]_D^{23}-113.1°$ (20 mg/ml, acetone).

EXAMPLE 24 d(+)-6-Formyl-2-benzylchroman

A. d(+)-2-Benzyl-6-hydroxymethylchroman

To a slurry of 934 mg (24.6 mmole) lithium aluminum hydride in 50 ml tetrahydrofuran (THF) was added dropwise a solution of 3.3 g (12.3 mmole) d(+)-2-benzylchroman-6-carboxylic acid, $[\alpha]_D^{23}+113.7°$ in 30 ml THF. Hydrogen gas was evolved and the reaction was mildly exothermic. The mixture was stirred at room temperature for two hours, cooled in ice, and water added carefully to decompose the excess hydride. The mixture was then diluted with 200 ml water, acidified and extracted with ethyl acetate. The extracts were washed with brine, dried (Na$_2$SO$_4$) and solvent evaporated in vacuo to give 3.3 g of oil, $[\alpha]_D^{23}+80.3°$ (20.13 mg/ml, acetone) which was used in the next step.

B. To a solution of 3.2 g (12.5 mmole) of the above product in 200 ml methylene chloride was added 33 g manganese dioxide and the mixture was stirred at ambient temperature for one hour. The mixture was filtered through diatomaceous earth and the filtrate evaporated in vacuo to yield 3.1 g of the desired aldehyde as a yellow oil, $[\alpha]_D^{23}+124.50°$ (20.53 mg/ml, acetone).

EXAMPLE 25 l(−)-6-Formyl-2-benzylchroman

A. l(−)-2-Benzyl-6-hydroxymethylchroman

Repeating the procedure of Example 24, Part A, with 1.35 g l(−)-2-benzylchroman-6-carboxylic acid, $[\alpha]_D^{23}-113.1°$, gave 1.30 g of product, $[\alpha]_D^{23}-79.25°$ (20 mg/ml, acetone) which was converted to aldehyde in the next step.

B. A mixture of 2.45 g (9.63 mmole) of the product of Part A, above, 24.5 g manganese dioxide and 200 ml methylene chloride was stirred at room temperature for 1.5 hours and the product isolated as in Example 23, Part B, to yield 2.23 g of the title compound, $[\alpha]_D^{23}-123.6°$ (20 mg/ml, acetone).

EXAMPLE 26

1-(2,3-Dihydrobenzofuran-5-yl)-1-thiazolidine-2,4-dione-5-yl)ethane (II, R=CH$_3$, R$_1$-R$_4$=H)

A. 5-Acetyl-2,3-dihydrobenzofuran

To a stirred solution of 12 g [100 mmole] 2,3-dihydrobenzofuran in 80 ml carbon disulfide was added in portions 30 g (225 mmole) anhydrous aluminum chloride. The mixture was heated at reflux and 18.9 ml (200 mmole) acetic anhydride was slowly added. Refluxing was continued for one hour after the addition was completed. Carbon disulfide was then removed by distillation and the residue was cooled in ice. Cracked ice (100 ml) was slowly added, the reaction mixture was acidified to pH 1 and diluted with water (100 ml) and extracted with ethyl ether (2×250 ml). The extracts were dried (Na$_2$SO$_4$) and the ether evaporated. The residual oil was purified pn a column of silica gel (600 ml), eluting with 9:1 (v/v) hexane/ethyl acetate, then with a 4:1 (v/v) mixture of the same solvents, and finally with a 2:1 mixture. The product fractions were combined and evaporated to obtain the desired product as an oil; $^1$H-NMR(CDCl$_3$)ppm(delta): 2.4 (s, 3H), 3.2 (t, 2H), 4.6 (t, 2H), 6.7 (d, 1H), 7.7 (m, 2H).

B. 5-[1-(2,3-Dihydrobenzofuran-5-yl)ethylidene]-thiazolidine-2,4-dione (III, R=CH$_3$, R$_1$-R$_4$=H)

A stirred mixture of 1.9 g (11.7 mmole) 5-acetyl-2,3-dihydrofuran, 1.37 g (11.7 mmole) thiazolidine-2,4dione and 1.92 g (23.4 mmole) anhydrous sodium acetate was heated in an oil bath at 160° C. for 20 minutes and then for 40 minutes at 190° C. After standing overnight at room temperature, the mixture was stirred with 75 ml water for 30 minutes, the water decanted and the residue stirred with 75 ml ethyl acetate for 18 hours. The mixture was filtered to yield 1.2 g of the desired unsaturated compound.

C. Hydrogenation of the unsaturated compound obtained in Part B by the method of Example 11 affords the title compound in like manner.

When propionic anhydride or propionyl chloride is employed in the procedure of Part A, above, 5-propionyl-2,3-dihydrobenzofuran is obtained. This, in turn, is converted to 5-[1-(2,3-dihydrobenzofuran-5-yl)propylidene]thiazolidine-2,4-dione (III, R=C$_2$H$_5$, R$_1$-R$_4$=H) which upon hydrogenation gives the corresponding saturated compound: 1-(2,3-dihydrobenzofuran-5-yl)-1-thiazolidine-2,4-dione-5-yl)propane (II, R=C$_2$H$_5$, R$_1$-R$_4$=H).

EXAMPLE 27

Tablets

A tablet base is prepared by blending the following ingredients in the proportion by weight indicated:

| Sucrose, U.S.P. | 80.3 |
| Tapioca starch | 13.2 |
| Magnesium stearate | 6.5 |

Into this tablet base there is blended sufficient sodium dl-5-[2-benzyl-3,4-dihydro-2H-benzopyran-6-yl)-methylthiazolidine-2,4-dione to form tablets containing 50 mg, 100 mg or 250 mg of active drug (weight equivalent to the free acid). The portion of blend to active drug is within the limits of 1-0.167 to 1-1, e.g., in the extremes, 62.0 mg of sodium salt dihydrate and 300 mg of blend in a 50 mg tablet or 310.0 mg of sodium salt dihydrate and 250 mg of blend in a 250 mg tablet.

EXAMPLE 28

Injectable Preparation

Sterile sodium d-5-[2-benzyl-3,4-dihydro-2H-benzopyran-6-yl)methyl thiazolidine-2,4-dione is dry filled into vials so as to contain 571.0 mg of the sodium salt per vial (equivalent to 550 mg of free acid). Prior to use, sterile water for injection (11 ml) is added, and the mixture shaken to form a solution, containing 50 mg/ml of active drug, which is suitable for intravenous, intramuscular or subcutaneous injection.

Alternatively, vials are filled by a freeze drying procedure. Two ml of a sterile, aqueous solution containing 286 mg/ml of sodium salt is introduced into each vial. The vials are freeze dried on trays.

PREPARATION A

5-Hydroxymethyl-2-methoxymethyl-2,3-dihydrobenzofuran (i) Ethyl 4-allyloxybenzoate To a stirred solution of 66.4 g (0.4 mole) ethyl 4-hydroxybenzoate in 100 ml acetone, under a nitrogen atmosphere was added 55.3 g (0.40 mole) finely powdered potassium carbonate and 53.2 g (0.44 mole) allyl bromide and the resulting mixture was heated at reflux overnight. After cooling to room temperature the mixture was filtered, washing with ethyl ether. The filtrate and washings were washed with water, brine and dried (MgSO$_4$). Evaporation of solvent in vacuo gave 82.3 g of product as a clear oil. $^1$H-NMR(CDCl$_3$)ppm(delta): 5.0-5.5 (m), 5.8 (m), 6.8 (m), 8.0 (m).

(ii) Ethyl 3-allyl-4-hydroxybenzoate

A mixture of 82.3 g (0.899 mole) ethyl 4-allyloxybenzoate in 100 ml N,N-dimethylaniline was stirred under nitrogen while heating at reflux for 2 days. The resulting mixture was cooled to room temperature, the solvent distilled in vacuo, the residue taken up in ethyl ether, washed three times with 1N hydrochloric acid and extracted with 1N sodium hydroxide solution. The alkaline extract was acidified to pH 3.0, extracted with ethyl ether and the extracts dried (MgSO$_4$). Evaporation of solvent provided 47.1 g of the desired product as a solid, TLC with 1.5:1 isopropyl ether/hexane gave one spot, Rf 0.2.

(iii) Ethyl 2-hydroxymethyl-2,3-dihydrobenzofuran-5-carboxylate

A mixture of 47.1 g (0.228 mole) ethyl 3-allyl4-hydroxybenzoate, 350 ml chloroform and 79.7 g (0.462 mole) m-chloroperbenzoic acid was heated at reflux, with stirring, under nitrogen for 3.5 hours. The resulting mixture was allowed to cool to room temperature, the solvent evaporated, the residue dissolved in ethyl ether, washed with 1N sodium hydroxide, brine and dried (MgSO$_4$). Evaporation of the ether gave 32.07 g of product as a colorless solid, m.p. 72°-77° C. which was used in the next step.

(iv) Ethyl 2-methoxymethyl-2,3-dihydrobenzofuran-5-carboxylate

A solution of 2.5 g (11.26 mmole) ethyl 2-hydroxymethyl-2,3-dihydrobenzofuran-5-carboxylate in 50 ml tetrahydrofuran was cooled under nitrogen to 0° C. and 595 mg (12.38 mmole) of a 50% by weight dispersion of sodium hydride in oil was added in portions. The mixture was stirred to 0° C. for 15 minutes, then a solution of 1.756 g (12.38 mmole) methyl iodide in 30 ml tetrahydrofuran was added dropwise. The resulting mixture was allowed to warm to room temperature and stirred overnight. The mixture was concentrated in vacuo, the residue partitioned between ethyl ether and water. The ether extracts were combined, washed with brine, dried (MgSO$_4$) and the solvent evaporated in vacuo to yield 2.28 g of product as an oil. $^1$H-NMR(CDCl$_3$) showed singlet at 3.4 ppm, consistent with the presence of a CH$_2$OC$\underline{H}_3$ group.

(v) To an anhydrous solution of 2.66 g (11.26 mmole) ethyl 2-methoxymethyl-2,3-dihydrobenzofuran-5-carboxylate in 15 ml tetrahydrofuran was added, in portions with stirring under nitrogen, 426 mg (11.26 mmole) lithium aluminum hydride and the mixture was stirred at room temperature for 2.4 hours. The reaction was quenched by cautious, dropwise addition of water, then acidified with 1N hydrochloric acid. The volatiles were evaporated and the residue taken up in water and extracted with ethyl ether, washing the extracts with brine. After drying over anhydrous magnesium sulfate and evaporation of solvent 1.674 g of oil was obtained. This crude product was dissolved in a small amount of methylene chloride and purified by column chromatography on silica gel to afford 1.40 g of product which was used as starting material in the procedure of Example 5.

PREPARATION B

Reduction of 444 mg (2 mmole) ethyl 2-hydroxymethyl-2,3-dihydrobenzofuran-5-carboxylate, Preparation A, Part (iii), in 15 ml tetrahydrofuran with lithium aluminum hydride, 155 mg (4 mmole), by the method of Preparation A, Part iv), afforded 0.3 g of 2,5-bis-hydroxymethyl-2,3-dihydrobenzofuran as an oil, TLC 1:2 ethyl acetate/hexane, Rf 0.2, iodine positive. $^1$H-NMR(CDCl$_3$)ppm(delta): 3.6 (CH$_2$OH at 2-position), 4.6 (CH$_2$OH at 5-position).

PREPARATION C

5-Hydroxymethyl-2-methyl-2,3-dihydrobenzofuran (i) Ethyl 2-bromomethyl-2,3-dihydrobenzofuran-5-carboxylate To a solution of 5.0 g (22.5 mmole) ethyl 2-hydroxymethyl-2,3-dihydrobenzofuran-5-carboxylate in 80 ml methylene chloride under nitrogen was added in one portion 6.5 (24.7 mmole) triphenylphosphine and the resulting solution was stirred for ten minutes. To this was added, in portions over twenty minutes, 4.39 g (24.7 mmole) N-bromosuccinimide and the resulting mixture was stirred overnight at room temperature. The mixture was diluted with methylene chloride, extracted with water, brine and dried (MgSO$_4$). Evaporation in vacuo afforded an oil which was triturated with ethyl ether and filtered to remove insoluble triphenylphosphine oxide. Evaporation of the filtrate yielded 8.4 g of crude product which was charged to a column containing 200 g silica gel and eluted with methylene chloride to provide 5.29 g of purified product, TLC Rf 0.85. Mass spectrum (m/e) 286 (M+). $^1$H-NMR(CDCl$_3$) ppm(delta): 3.2 (CH$_2$Br), 3.6 (benzyl CH$_2$).

(ii) Ethyl 2-methyl-2,3-dihydrobenzofuran-5-carboxylate

To a solution of 1.18 g (4.1 mmole) of the above 2-bromomethyl compound in 15 ml anhydrous benzene under nitrogen was added 1.96 ml (7.45 mmole) tri-n-butyltin hydride and the mixture stirred at room temperature for 45 minutes, then heated at 60°–65° C. with an additional increment of tri-n-butyltin hydride, 1 ml, and a second increment of 1.9 ml after 4 hours. Heating was continued for 70 hours. The mixture was concentrated to dryness in vacuo and the residual oil purified by chromatography on silica gel, eluting with 100% hexanes, to afford 1.09 g of product. TLC with 4:1 hexane/ethyl ether showed product with Rf 0.4 and residual tributyltin bromide (Rf 0.8).

(iii) To a solution of 853 mg (4.14 mmole) ethyl 2-methyl-2,3-dihydrobenzofuran-5-carboxylate in 9 ml dry tetrahydrafuran under nitrogen was added 157 mg (4.14 mmole) lithium aluminum hydride in portions and the resulting mixture was stirred at room temperature overnight. The mixture was worked up as described in Preparation A, Part (v), to afford 752 mg of product. The NMR spectrum showed the presence of a band at 4.5 ppm, characteristic of a benzyl alcohol CH$_2$ group. TLC with 1:1 hexane/ethyl ether showed one spot at Rf 0.2 (vanillin spray).

PREPARATION D

3-Benzyl-2,3-dihydrobenzofuran (i) 2,3-Dibromo-2,3-dihydrobenzofuran

A solution of 40.8 g (345 mmole) 2,3-benzofuran in 180 ml carbon disulfide under nitrogen at −12° to −15° C. was added to a solution of 55.6 g (348 mmole) bromine in 150 ml carbon disulfide at a rate sufficient to keep the temperature below −5° C. When the addition was completed, the mixture was stirred at −10° C. for 30 minutes, then warmed to room temperature. The product was collected by filtration and washed with hexane to yield 37.2 g as a first crop. Evaporation of the mother liquors gave an additional 50.3 g of solid product. $^1$H-NMR(CDCl$_3$)ppm(delta): 5.7 (s, 1H), 6.9–7.6 (m, 5H). Total yield 87.5 g (91%).

(ii) 3-Bromo-2,3-benzofuran

To a cooled solution of 21.6 g (327 mmole) 85% potassium hydroxide in 145 ml ethanol was added, in four portions at 0° C., 50.3 g 2,3-dibromo-2,3-dihydrobenzofuran. The mixture was warmed to room temperature over 30 minutes, stirred at 80° C. (bath temperature) for two hours, then cooled to room temperature. The reaction mixture was filtered, washing with ethanol, the filtrate concentrated in vacuo, the residue taken up in 200 ml water and extracted with ethyl ether. The extract was dried (Na$_2$SO$_4$) and the ether evaporated to obtain 18 g (50%) of the desired product which was used in the next step.

(iii) 3-Benzyl-2,3-benzofuran

A solution of 18 g (91.4 mmole) of the 3-bromo compound, above, in 175 ml dry ethyl ether was cooled under nitrogen to −70° C. and 64.8 ml (100 mmole) of 1.55M n-butyllithium in hexane was added dropwise. When the addition was completed, the mixture was stirred at −70° C. for 30 minutes, then warmed to room temperature over one hour. The mixture is again cooled to −70° C., a solution of 11.6 g (91.4 mmole) benzyl chloride in 25 ml ethyl ether was added dropwise, the mixture allowed to warm to room temperature then heated at reflux for 20 hours. The mixture was cooled, quenched with water, 100 ml water added and extracted with ethyl ether. The ether layers were dried (Na$_2$SO$_4$) and concentrated to afford 19.5 g of product as an oil which was used in the next step.

(iv) To a solution of 19.5 g (91.4 mmole) 3-benzylbenzofuran in 75 ml trifluoroacetic acid was added 31.8 g (273 mmole) triethylsilane and the mixture was heated at reflux for six hours. The mixture was concentrated in vacuo, the residue diluted with water and extracted with ethyl ether. The ether extracts were carbon treated, the filtrate dried (Na$_2$SO$_4$) and the solvent evaporated to provide a dark oil. The oil was purified by silica gel column chromatography eluting with hexane, then its mixtures with ethyl ether. The combined product fractions were evaporated to provide 3.9 g (20%) of the title compound as a yellow oil. $^1$H-NMR(CDCl$_3$)ppm(delta): 3.2 (m, 2H), 4.0 (m, 2H), 4.6 (t, 1H), 6.7–7.5 (m, 9H).

PREPARATION E

2-Benzyl-2,3-dihydrobenzothiophene (i) 2-Benzyl-2,3-benzothiophene

To a solution of 26.8 g (0.20 mole) thianapthene in 250 ml ethyl ether at 15° C. was added 130 ml (0.208 mole) 1.6M n-butyl lithium in hexane. When the addition was completed, the mixture was warmed to room temperature, stirred for one hour, cooled to 0° C. and 23 ml (0.20 mole) benzylchloride was added dropwise at 0°-2° C. The mixture was then stirred for one hour at room temperature and heated at reflux for five hours. Water was then added slowly with cooling, the ether layer separated, washed with water and the ether evaporated to afford 50 g of oil. The oil was distilled at 12-15 mm Hg. to obtain two fractions up to 160° C. containing starting thianapthene. The residue (20 g) was crystallized from hexane to obtain 3.9 g of product, m.p. 82°-84° C. Another 3.4 g of product was obtained from the mother liquors.

(ii) A suspension of 605 mg (2.7 mmole) 2-benzyl-2,3-benzothiophene, 4 ml trifluoroacetic acid and 2.15 ml triethylsilane was heated at 58°-60° C. (bath temperature) for six hours. The volatiles were distilled at 12-15 mm and pot temperature up to 110° C. The residue was dissolved in ethyl ether, washed with water (10 ml), 0.5N sodium hydroxide (5 ml), water again (10 ml), and the organic layer concentrated in vacuo to obtain 550 mg residual oil. M.S. (m/e): 226 (M+), 224, 135 (base).

In a second run starting with 7.3 g (0.035 mole) of 2-benzyl-2,3-benzothiophene and purification of the crude residue by silica gel chromatography, eluting with hexane, afforded 5.96 g of the desired product. $^1$H-NMR (CDCl$_3$)ppm(delta): 2.8-3.3 (m, 2H), 3.8-4.3 (m, 1H).

(iii) 2-Methyl-2,3-dihydrobenzothiophene

Repeating the procedure of Part (i), above, but with methyl p-toluenesulfonate in place of benzyl chloride gave 2-methyl-2,3-benzothiophene as a yellow oil which crystallized upon standing. Distillation gave a white solid in 89.5% yield which was 90% pure by NMR.

This was reduced by the method of Part (ii) to afford 2-methyl-2,3-dihydrobenzothiophene in 77% step yield after purification on a silica gel column, eluting with hexane. Rf 0.35 (TLC, hexane).

(iv) 2-Cyclohexylmethyl-2,3-dihydrobenzofuran

By employing equimolar amounts (0.141 mole) of 2,3-benzofuran, n-butyllithium and cyclohexylmethyl bromide in the procedure of Part (i), above, gave 2-cyclohexylmethyl-2,3-benzofuran in 26% yield as a yellow liquid b.p. 111°-115° C. at 0.8 Torr, M.S. (m/e): 214 (M+), 131 (base).

This was reduced by the method of Part (ii), above, to provide the title compound as a yellow oil in 99% yield.

(v) 2-(4-Fluorophenyl)methyl-2,3-dihydrobenzofuran

Similarly employing equimolar amounts of 4-fluorophenylmethyl bromide, 2,3-benzofuran and n-butyllithium gave 2-(4-fluorophenyl)methyl-2,3-benzofuran as a pale red liquid, b.p. 130°-132° C. at 0.7 Torr in 40% yield. M.S. (m/e): 226 (M+). This was reacted with triethylsilane in trifluoroacetic acid by the method of Part (ii), above, to afford the desired dihydrobenzofuran in 98% yield. M.S. (m/e): 228 (M+), 119 (base).

PREPARATION F

5-Bromo-2-ethoxyethyl-2,3-dihydrobenzofuran (i) 2-Ethoxyethyl-2,3-benzofuran

To a solution of 11 ml (0.1 mole) 2,3-benzofuran in 150 ml tetrahydrofuran was added 71 ml (0.11 mole) n-butyllithium in hexane (1.55M) over 30 minutes at 27°-32° C. and the mixture stirred at room temperature for 1.5 hours. A solution of 12.4 ml (0.11 mole) 2-bromoethylethyl ether in ethyl ether (20 ml) was added at 27°-35° C. and the resulting mixture stirred overnight at room temperature. Water (100 ml) was slowly added and the mixture extracted with ethyl ether, washed with water and the ether layer concentrated in vacuo to provide 18.8 g of residual oil which was distilled at 10-12 Torr to provide 10.7 g of product, b.p. 135° C. TLC Rf 0.30 (10:1 hexane/ethyl acetate). M.S. (m/e): 190 (M+).

(ii) 2-Ethoxyethyl-2,3-dihydrobenzofuran

To a solution of 10.6 g (0.056 mole) of the product obtained in Part (i) in 100 ml acetic acid was added 2 g 10% palladium-on-carbon catalyst and the mixture hydrogenated at 3 bars pressure overnight. The mixture was then filtered and the filtrate concentrated to dryness in vacuo to provide 10.6 of the desired product as an oil. $^1$H-NMR(CDCl$_3$)ppm(delta): 4.6-5.1 (m, 1H).

(iii) A solution of 5.76 g (0.03 mole) of the above product in 75 ml carbon tetrachloride was cooled to 0° C. and 1.55 ml (0.03 mole) bromine in 5 ml of the same solvent was added at 0° C. The resulting mixture was stirred for 20 minutes, allowed to warm to room temperature, washed with water, sodium bicarbonate solution and the solvent evaporated in vacuo to afford 7.8 g of the title compound as an oil. The oil was purified by passing it through a silica gel column, eluting with 10:1 hexane/ethyl acetate, to yield 2.7 g of pure product. $^1$H-NMR(CDCl$_3$)ppm(delta): 6.5-6.65 (d, 1H), 7.1-7.4 (2H).

PREPARATION G

Spiro[5-bromo-2,3-dihydrobenzofuran-2,1'-cyclohexane]

(i) (5-Bromo-2-hydroxyphenyl)cyclohexylmethanol

A solution of 3.35 g (0.0167 mole) 5-bromo-2-hydroxybenzaldehyde in 15 ml dry tetrahydrofuran (HF) was cooled to −78° C. To this was added dropwise over seven minutes, a solution of 9.37 g (0.050 mole) cyclohexylmagnesium bromide (prepared by reaction of cyclohexylbromide with an equimolar amount of magnesium turnings in THF under anhydrous conditions) in THF (50 ml). The reaction mixture was stirred at −78° C. for 1.5 hours, then at −10° C. for another hour. The reaction was quenched by addition of 3.0 g (0.050 mole) acetic acid, the mixture allowed to warm slowly to room temperature and stirred for 70 hours. Evaporation of solvent gave a viscous oil which was partitioned between 500 ml ethyl acetate and 300 ml 1N hydrochloric acid. The organic layer was washed with saturated sodium bicarbonate (2×300 ml), brine, dried (MgSO$_4$), filtered and solvent evaporated in vacuo to yield 7.0 g of product as a viscous oil. The oil was purified by silica gel chromatography, eluting with 4:1 hexane/ethyl acetate to obtain 3.7 g (78%) of product which crystallized upon standing, m.p. 110-113° C. M.S. m/e): 286, 284, 268, 266, 201 (base).

(ii) A mixture of 3.4 g (0.012 mole) (5-bromo-2-hydroxyphenyl)cyclohexylmethanol, 100 ml acetic acid and 1 ml concentrated sulfuric acid was heated at 90° C. for 16 hours. The mixture was concentrated in vacuo and the residual oil partitioned between ethyl acetate and saturated sodium bicarbonate solution. The organic layer was washed again with bicarbonate solution, brine, dried (MgSO$_4$), filtered and concentrated to dryness in vacuo. The residual oil which crystallized upon standing, gave 3.1 g (97%).

PREPARATION H

3-Phenyl-2,3-dihydrobenzofuran (i) 3-Phenyl-2,3-dihydrobenzofuran-2-one

To an ice-cooled mixture of finely pulverized phenol (26.5 g, 0.282 mole) and dl-mandelic acid (30.45 g, 0.200 mole) was added 80 ml of 70% (v/v) sulfuric acid and the mixture stirred at 0° C. for 5 minutes, then heated at 115° C. for 45 minutes. The reaction mixture was cooled, poured onto 400 ml icewater and extracted with methylene chloride. The organic layers were washed with sodium bicarbonate solution, dried ($Na_2SO_4$) and concentrated to obtain a clear oil which crystallized to a colorless solid, m.p. 109°-111° C., 15.1 g (36% yield). $^1$H-NMR($CDCl_3$)ppm (delta) 4.8 (s, 1H), 7.2 (m, 9H).

(ii) 2(2-Hydroxy-1-phenylethyl)phenol

To an ice-cooled suspension of 3.55 g (88.9 mmole).95% lithium aluminum hydride in 200 ml dry ethyl ether was slowly added a solution of 15 g (71.4 mmole) of the product of Part (i) in 100 ml dry ether and the resulting mixture stirred for 30 minutes at 25° C. It was cooled to 0°-5° C., quenched by dropwise addition of 4 ml water, 4 ml 15% (w/v) sodium hydroxide solution and 12 ml water. The resulting mixture was filtered through diatomaceous earth, the organic layer separated and washed with brine, dried ($Na_2SO_4$) and concentrated to dryness to give 2.0 g of oil. The filter cake was stirred with 400 ml ethyl acetate for one hour, filtered again and the filtrate concentrated to afford 8.1 g of oil which was combined with the above 2 g for use in the next step. $^1$H-NMR ($CDCl_3$)ppm(delta): 4.2 (m, 3H), 6.8 (m, 4H), 7.1 (s, 5H).

(iii) A solution of 10 g (46.7 mmole) of the oil obtained in Part [ii] and 12.24 g (46.7 mmole) triphenylphosphine in 125 ml dry tetrahydrofuran (THF) was cooled in an ice bath. A solution of 7.35 ml (8.13 g, 46.7 mmole) diethylazodicarboxylate (d=1.106) in 20 ml THF was added at 10° C. The resulting mixture was stirred at room temperature for one hour, the solvent evaporated in vacuo and the residue stirred in 100 ml ethyl ether for 90 minutes. The mixture was filtered and the filtrate concentrated to provide an oily residue which was purified by chromatography on silica gel, eluting with 5% ethyl acetate in hexane. The product fractions gave 6.4 g of clear oil (70% yield).

PREPARATION I

2-Benzyl-2,3-dihydrobenzofuran

To a solution of sodium ethoxide prepared from 28 g sodium metal and 500 ml absolute ethanol was added 122 g (1 mole) salicylaldehyde and 200 ml dimethylformamide. The mixture was heated to 80° C. Then 200 g (1 mole) alpha-bromoacetophenone was added in small portions. The mixture was stirred at reflux for 1.5 hours after which the ethanol was distilled. The residue was cooled and partitioned between 750 ml water and 750 ml ethyl acetate. The organic layer was washed twice with 400 ml portions of 1N sodium hydroxide, water (2×300 ml), dried ($Na_2SO_4$), concentrated to one-third volume, filtered to remove precipitated product which was washed with ethyl ether to yield 75.8 g of 2-benzoylbenzo(b)furan as pink crystals, m.p. 88°-90° C.

To a solution of 22 g (0.1 mole) of 2-benzoylbenzo(b)furan in 250 ml acetic acid was added 3 g 10% Pd/C catalyst and the mixture hydrogenated at 3 atmospheres pressure, with shaking for 70 hours. The mixture was filtered and the filtrate concentrated in vacuo to obtain 19.4 g (92%) of the desired product.

PREPARATION J 2-n-Butyl-2,3-dihydrobenzofuran (i) 2-n-butyrylbenzo(b)furan

A mixture of 25 g (217 mmole) benzo(b)furan, 32.9 g (208 mmole) n-butyric anhydride, 20.8 g (236 mmole) n-butyric acid and 6.25 g of phosphoric acid (85%, d=1.685) was stirred while heating at reflux (130° C.) four hours and allowed to stand overnight. The cold mixture was made alkaline with 1N sodium hydroxide (1200 ml), extracted with methylene chloride, the extracts dried ($Na_2SO_4$) and solvent evaporated. The residue was distilled in vacuo to obtain 19.6 g of product, b.p. 170°-175° C., 15 Torr, which solidified upon cooling.

(ii) 2-n-Butylbenzo(b)furan

A mixture of 34.7 g (184 mmole) of 2-n-butyrylbenzo(b)furan, 47.8 g hydrazine hydrate and 90 ml diethylene glycol was heated at 100° C. for 5 minutes, 31.1 g (471 mmole) potassium hydroxide was added and the mixture heated at reflux for two hours. The mixture was diluted with 300 ml water, extracted with ethyl ether, the extracts washed with 1N hydrochloric acid, water, dried and the solvent evaporated in vacuo. The residual oil (25.1 g) was purified by chromatography on silica gel, eluting with hexane to provide 16.3 g of product. $^1$H-NMR($CDCl_3$)ppm(delta): 0.9 (t, 3H), 1.5 (m, 4H), 2.4 (t, 2H), 6.2 (s, 1H), 6.9-7.5 (m, 4H).

(iii) Reduction of 15 g (86.0 mmole) of the above product with triethylsilane in trifluoroacetic acid by the method of Preparation D, Part (iv), and purification of the crude product on a silica gel column, eluting with hexane and hexane containing 5% ethyl acetate and distillation of the combined product fractions gave 15.5 g of the title compound as a clear oil, b.p. 114°-120° C. 15 Torr. M.S. (m/e): 176 (M+), TLC Rf 0.55, hexane.

PREPARATION K

6-Bromo-2-cyclohexyl-3,4-dihydro-2H-benzopyran (i) 6-Bromo-2-chromanone

To a solution of 74.08 g (0.50 mole) 2-chromanone in 150 ml carbon disulfide at 0° C. was added dropwise over 15 minutes, 79.91 g (0.50 mole) bromine. Stirring was continued at 0° C. for ten minutes and at room temperature for 2 days. The resulting mixture was filtered, the crystals air dried to afford 96.8 g (85%) of colorless material, m.p. 103°-105° C. (2 crops).

(ii) 6-Bromo-2-chromanol

To a mixture of 16.4 g (72.2 mmole) 6-bromo-2chromanone and 60 ml dry tetrahydrofuran, under nitrogen at −70° C., was added a cloudy solution of 18.4 g (72.2 mmole) lithium hydrido-tri(t-butoxy)aluminate (commercial) over 30 minutes. The mixture was stirred while allowing it to warm to room temperature over 90 minutes, then poured onto 250 ml ice/water. The resulting mixture was filtered, the cake washed with ethyl ether, then ethyl acetate and the organic phase is separated. The aqueous layer is extracted with ethyl acetate, the organic layers combined, dried ($Na_2SO_4$) and solvent evaporated to obtain 9.5 g crude product. An additional 4 g was obtained by reworking the filter cake, above. The combined crude products were purified on a silica gel column, eluting with 9:1 hexane/ethyl acetate, then a 4:1 mixture of the same solvents to obtain the purified product as an oil, 5.6 g.

(iii) A solution of cyclohexylmagnesium bromide in ethyl ether (55 ml) was prepared from 15.6 g (96 mmole) cyclohexyl bromide and 2.56 g magnesium. This was added dropwise to a solution of 5.5 g (24 mmole) 6-bromo-2chromanol in 55 ml dry tetrahydrofuran, under nitrogen at −70° C. The reaction mixture was stirred at −78° C. for two hours, then at 0° C. for one hour and quenched by addition of 4.1 ml acetic acid. The solvents were evaporated in vacuo, the residual white gel diluted with 250 ml ethyl acetate, washed with 1N hydrochloric acid (100 ml), saturated sodium bicarbonate solution, and dried ($Na_2SO_4$). Evaporation of solvent afforded an oil which solidified upon trituration with hexane, 5.3 g, m.p. 124°–126° C. This was identified as the diol, 1-cyclohexyl-3-(2-hydroxy-5-bromophenyl)propanol. The diol was dissolved in 125 ml acetic acid, 2.5 ml concentrated sulfuric acid added and the mixture heated at reflux for 16 hours. After evaporation in vacuo, the residue was diluted with ethyl acetate, washed with saturated sodium bicarbonate, dried ($Na_2SO_4$), carbon treated, the solution evaporated and passed through a silica gel column, eluting with hexane to yield 1.45 g of the title compound as an oil. The structure was verified by $^1$H-NMR spectroscopy.

(iv) 6-Bromo-2-phenylmethyl-3,4-dihydro-2H-benzopyran

By repeating the procedure of Part (iii), but with benzylmagnesium chloride in place of cyclohexylmagnesium bromide, and employing tetrahydrofuran as solvent gave a 96% yield of crude 1-phenyl-4-(5-bromo-2-hydroxyphenyl)-2-butanol which was purified by column chromatography on silica gel to provide 4.3 g (34%) of purified diol as a white solid. Treatment with sulfuric/acetic acid as above gave 4.2 g of product as a crude oil which was purified on a silica gel column to provide 2.1 g (54% step yield) of the desired benzopyran as an amber oil. The $^1$H-NMR spectrum was consistent with the structure for the title compound.

(v) 6-Bromo-2-cyclohexylmethyl-3,4-dihydro-2H-benzopyran

By use of cyclohexylmethylmagnesium bromide in the procedure of Part (iii) gave 25% (2.2 g) of purified diol, 1-cyclohexyl-4-(5-bromo-2-hydroxyphenyl)-2-butanol as a white solid which was cyclized as above to afford 1.15 g .5(5%) of the desired benzopyran as a yellow oil which was used as starting material for preparation of the corresponding benzopyran-6-carboxaldehyde.

PREPARATION L

Spiro[Benzopyran-3(2H), 1'-cyclohexane]

(i) 2-Benzyloxybenzyl chloride

To a solution of 46.5 (0.217 mole) 2-benzyloxybenzyl alcohol (prepared by reaction of 2-hydroxybenzyl alcohol with benzyl chloride in ethanol containing an equimolar amount of potassium t-butoxide at 100° C.) in 100 ml chloroform was added 17.2 g (0.217 mole) pyridine followed by dropwise addition of a solution of 25.8 g (0.217 mole) thionyl chloride in 60 ml chloroform. The resulting mixture was heated at reflux for 1.5 hours, cooled, washed with water, brine and dried ($MgSO_4$). Evaporation of solvent gave 45.8 g crude oil which was distilled in vacuo to yield 40.7 g (81%) of product as a colorless oil, b.p. 141° C.(1 Torr).

(ii) Methyl 1-(2-benzyloxyphenyl)methylcyclohexan-1-carboxylate

Under anhydrous conditions and a nitrogen atmoshere a solution of 8.7 g (0.086 mole) diisopropylamine in 250 ml tetrahydrofuran was cooled to −78° C. and 1.6M n-butyllithium (53.75 ml, 0.086 mole) was added dropwise over ten minutes. The mixture was stirred for 45 minutes, allowed to warm to 0° C. and 12.2 g (0.086 mole) methyl cyclohexancarboxylate was added. Stirring was continued for 45 minutes and then 20 g (0.086 mole) 2-benzyloxybenzyl chloride in 20 ml tetrahydrofuran was added dropwise. The resulting mixture was stirred at room temperature for 24 hours, quenched by addition of 150 ml 3M acetic acid and stirred at room temperature for one week. The mixture was diluted with ethyl ether, washed with sodium bicarbonate solution, brine, dried ($MgSO_4$) and concentrated to a yellow oil, 29.3 g. This was distilled to obtain 20.23 g (70%) of viscous oil, b.p. 135°–140° C. (0.4 Torr).

(iii) 1-Hydroxymethyl-1-(2-hydroxyphenyl)methylcyclohexane

A solution of 10 g (0.030 mole) of the methyl ester obtained in Part (ii) in 100 ml toluene was cooled in ice and 10.6 ml of 3.4M sodium bis(2-methoxyethoxy)aluminum hydride in toluene was added dropwise over seven minutes and the resulting mixture stirred at room temperature for 24 hours. The reaction was quenched by cautious addition of water (12 ml), filtered and washed with toluene. The filtrate was diluted with an equal volume of ethyl acetate, washed with 1N sodium hydroxide, brine, dried ($MgSO_4$) and concentrated in vacuo to a yellow oil, 9.3 g, which was identified as 1-hydroxymethyl-1-(2-benzyloxyphenyl)methylcyclohexane. This was dissolved in 150 ml dry ethanol, 600 mg 10% palladium-on-carbon catalyst was added and the mixture hydrogenated with agitation at 3.5 kg/cm$^2$ pressure for 18 hours. The catalyst was removed by filtration, the filtrate concentrated in vacuo to afford 5.4 g (83%) of the desired diol as a pink solid. The $^1$H-NMR spectra was consistent with the structure of the title compound.

(iv) To a solution of 4.73 g (0.0215 mole) in 175 ml dry tetrahydrofuran, under nitrogen at 0° C. was added 5.63 g (0.0215 mole) triphenylphosphine and 3.74 g (0.0215 mole) ethyl azodicarboxylate and the mixture stirred overnight at room temperature. Evaporation of solvent and silica gel chromatography of the residue, eluting with 14:1 hexane/ethyl acetate afforded 4.0 g (92%) of the title spiro compound, the structure of which was verified by $^1$H-NMR spectroscopy.

PREPARATION M

6-Hydroxymethyl-3,4-dihydro-2H-benzopyran (i) 3-Bromopropyl(2,4-dibromophenyl)ether A mixture of 15.1 g (60 mmole) 2,4-dibromophenol, 16.1 g (80 mmole) 1,3-dibromopropane, 2.6 g sodium hydroxide in 46 ml water was heated at reflux for two days, diluted with ethyl acetate and the separated organic phase washed with water, brine and dried ($MgSO_4$). Evaporation of solvent gave 22 g of crude which was purified on a silica gel column, eluting with methylene chloride to obtain 18.3 g of the desired tribromoether; Mass spectrum (m/e): 372 (M+).

(ii) Methyl 3,4-dihydro-2H-benzopyran-6-carboxylate

A solution of 17.2 g of the above tribromo ether in 305 ml dry tetrahydrofuran and 77 ml hexane was cooled to −90° C. and 32.8 ml 1.6M n-butyl lithium in hexane was added. The resulting mixture was stirred at −90° to −85° C. for two hours, allowed to warm to room temperature, then heated at reflux for one hour.

The mixture was cooled again to −85° C., a second 32.8 ml n-butyl lithium added. Carbon dioxide was then bubbled into the mixture for 10 minutes. After warming to room temperature, the reaction was quenched with 10% aqueous sodium carbonate, the layers separated, the aqueous phase acidified to pH 3.0, extracted with ethyl acetate to obtain 9.1 g of crude carboxylic acid which was purified on a silica gel column, eluting with methylene chloride to provide 7.5 g of pure acid. This was esterified by dissolving it in methanol, bubbling in dry hydrogen chloride for 30 seconds and stirring the resulting solution for 18 hours. Evaporation of solvent and distillation of the residual oil gave 5.1 g of the desired ester which was identified by its $^1$H-NMR spectrum.

(iii) To a solution of 2.0 g (10 mmole) of the above methyl ester in 75 ml dry tetrahydrofuran was added 374 mg lithium aluminum hydride and the mixture was stirred under nitrogen for 30 minutes. Water (1 ml) was added, the mixture partitioned between ethyl ether and water, the organic phase washed with brine and dried (MgSO$_4$). Evaporation of solvent gave 1.85 g of crude oil which was purified by silica gel column chromatography, eluting with 1:1 ethyl ether/hexane. The product fractions amounted to 1.19 g. Mass spectrum (m/e): 164 (M+).

(iv) By repeating the above procedures, but starting in Part (i) with 14-dibromobutane in place of 1,3-dibromopropane afforded 7-hydroxymethyl benzo(b)-2,3,4,5-tetrahydro-1-oxepin. In step (i) the tribromoether was obtained in 89% yield; in step (ii) the free acid was obtained in 72% yield, m.p. 163°–165° C., purified on silica gel column, m.p. 168°–169° C. The acid was not esterified, but was reduced directly by the method of Part (iii) in 94% yield to obtain the above benzoxepin as on oil. Mass spectrum (m/e): 178 (M+).

PREPARATION N

2-Cyclohexyl-2,3-dihydrobenzofuran (i) o-Hydroxybenzyltriphenylphosphonium bromide A solution of 26.23 g (0.10 mole) triphenylphosphine in 100 ml toluene at 0°–5° C. was perfused with HBr gas for 20 minutes, 250 ml ethyl ether was added and the mixture stirred for 20 minutes. The mixture was filtered, the white solid cake slurried in ether (500 ml), filtered again and air-dried to obtain 33.2 g (97%) of triphenylphosphonium bromide, m.p. 203°–205° C. (decomp.). In a separate flask 33 g (0.096 mole) of this salt, 11.9 g (0.096 mole) o-hydroxybenzyl alcohol and 100 ml dry acetonitrile were combined and heated at reflux for two hours. The resulting solution was cooled, filtered, the cake washed with 100 ml acetonitrile and dried in vacuo at 120° C. to obtain 26.2 g (61%) of the desired product, m.p. 223°–225° C. Mass spectrum (m/e): 368, 291, 262, 107.

(ii) 2-Cyclohexylbenzofuran

A mixture of 13 g (0.0289 mole) of the above product, 8.77 g triethylamine and 4.66 g (0.0318 mole) cyclohexylcarbonyl chloride and 120 ml toluene was heated at reflux under nitrogen for six hours, cooled, filtered to remove insoluble matter and the filtrate concentrated in vacuo. The residual solid was flash chromatographed, eluting with hexane to obtain 4.7 g (81%) of white crystals, m.p. 32°–34° C. Mass spectrum (m/e): 200 (M+).

(iii) To a solution of 4.7 g (0.0235 mole) of the product of Part (ii) in 10.7 g (0.094 mole) trifluoroacetic acid was added 5.46 g (17.5 ml, 0.047 mole) triethylsilane and the mixture heated at 65° C. for four hours. After pouring into water (500 ml) and extracting with ethyl ether (3×200 ml), the combined organic layers were washed with 1N sodium hydroxide, brine and dried (MgSO$_4$). Evaporation of solvent gave 5.37 g of soft colorless solid which crystallized upon standing, m.p. 56°–59° C. Mass spectrum (m/e): 202 (M+), 107.

(iv)a. When the above steps were repeated, but employing 1-methylcyclohexylcarbonyl chloride in Step (ii) gave 2-(1-methylcyclohexyl)benzofuran as a clear oil in 55% step yield. Mass spectrum (m/e): 214 (M+), 119. This was reduced by the method of Step (iii) to provide 2-(1-methylcyclohexyl)-2,3-dihydrobenzofuran in 99% step yield, m.p. 60°–63° C. Mass spectrum (m/e): 216 (M+).

b. Similarly, use of o-fluorophenylacetyl chloride in Step (ii) gave a 17% yield of 2-(2-fluorophenylmethyl)-benzofuran after purification by silica gel chromatography, viscous oil. Mass spectrum (m/e): 226 (M+), 131. This was reduced by the method of Step (iii) in 99% yield to obtain 2-(2-fluorophenylmethyl)-2,3-dihydrobenzofuran as a viscous oil. Mass spectrum (m/e): 228 (M+), 119.

c. Likewise use of 4-tetrahydro-2H-pyrancarbonyl chloride gave 2-tetrahydro-2H-pyran-4-ylbenzofuran in 71% yield, m.p. 64°–68° C. $^1$H-NMR(CDCl$_3$)ppm(delta): 1.8 (m, 1H), 3.5 (m, 4H), 4.0 (m, 2H), 6.3 (s, 2H), 7.4 (m, 1H). Reduction gave the corresponding 2,3-dihydrobenzofuran in quantitative yield as a white solid.

d. Also, use of 2-methyl-2-phenylpropionyl chloride in Part (ii), above, afforded a 62% yield of 2-(1-methyl-1-phenyl)ethylbenzofuran after purification by flash chromatography. $^1$H-NMR(CDCl$_3$)ppm(delta): 1.7 (s, 6H), 6.4 (s, 1H), 7.2 (m, 9H). This was reduced, as above, to afford 2-(1-methyl-1-phenyl)ethyl-2,3-dihydrobenzofuran in quantitative yield as an amber oil.

PREPARATION O

2,3-Dihydro-1-benzothiophene (i) 1,1-Dioxo-1-benzothiophene

A solution of 40 g (0.298 mole) 1-thianaphthene in 240 ml acetic acid was mixed with 180 ml 30% hydrogen peroxide and the mixture brought to reflux with an efficient condenser. The reaction is exothermic for a few minutes. Heating was continued for 15–20 minutes, the mixture was diluted with 800 ml water and cooled in ice for one hour. The precipitated product was collected by filtration and dried to obtain 32.8 g (66%) of the desired sulfone, m.p. 139°–140° C.

(ii) 2,3-Dihydro-1,1-dioxo-1-benzothiophene

To a solution of 22.8 g of 1,1-dioxo-1-benzothiophene in 100 ml ethanol and 150 ml dry tetrahydrofuran was added 800 mg 10% palladium-on-carbon and the mixture hydrogenated until hydrogen uptake ceased (about one hour). The qatalyst was removed by filtration and the filtrate evaporated to provide the reduced sulfone, 22.3 g (97%), m.p. 89°–90° C.

(iii) A solution of 22.3 g (132 mmole) of the product of Part (ii) in 200 ml tetrahydrofuran was added dropwise with stirring to a mixture of 5.81 g (145 mmole) lithium aluminum hydride (95%) in 400 ml dry ethyl ether, at a rate sufficient to maintain gentle reflux. Refluxing was continued for 30 minutes. The mixture was cooled in ice and quenched by cautious addition of 6 ml water followed by 6 ml 15% (w/v) sodium hydroxide and 18 ml water. The resulting mixture was filtered, the organic phase washed with brine, dried (Na$_2$SO$_4$) and evaporated to provide a yellow oil which was distilled to yield 10.4 g (58%) product, b.p. 129°–131° C. The structure was verified by $^1$H-NMR spectroscopy.

PREPARATION P

Thiochroman

Reduction of thiochroman-4-one with lithium aluminum hydride by the method of Preparation O, Part (iii), affords thiochroman-4-ol in like manner. This is taken up in acetic acid containing a molar excess of acetic anhydride, the mixture heated at reflux for three hours, cooled, ethanol added to quench the excess anhydride and the mixture hydrogenated by the method of Example 11.

We claim:

1. A compound of the formula

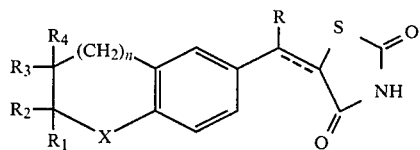

or a pharmaceutically acceptable cationic salt thereof, wherein the broken line is a bond or no bond, n is zero, 1 or 2;

X is O, S,

S or S=O;

R is H, CH$_3$ or C$_2$H$_5$;

when taken separately, R$_1$ is H, (C$_5$–C$_7$)cycloalkyl, (C$_6$–C$_8$) methylsubstituted cycloalkyl, pyridyl, thienyl, furyl, naphthyl, p-biphenylyl, tetrahydrofuranyl, tetrahydrothienyl, tetrahydropyranyl, C$_6$H$_4$W$_2$ or alk-W$_1$ and alk is (C$_1$–C$_6$)alkylene, ethylidene or isopropylide; W$_1$ is H, OH (C$_1$–C$_4$) alkoxy, (C$_1$–C$_4$)thioalkyl, pyridyl, furyl, thienyl, tetrahydrofuryl, tetrahydrothienyl, naphthyl, (C$_5$–C$_7$)cycloalkyl or C$_6$H$_4$W$_2$ and W$_2$ is H, OH, F, Cl, Br, (C$_1$–C$_4$)alkyl, (C$_1$–C$_4$)alkoxy or (C$_1$–C$_4$)thioalkyl; R$_2$ is H or CH$_3$, R$_3$ is H, (C$_1$–C$_6$)alkyl, C$_6$H$_4$W$_2$ or benzyl; and R$_4$ is H;

when R$_3$ and R$_4$ are taken together they form (C$_4$–C$_6$) alkylene and R$_3$ and R$_4$ are each H;

when R$_3$ and R$_4$ are taken together they form (C$_4$–C$_6$) alkylene and R$_1$ and R$_2$ are each H; and when R$_2$ and R$_3$ are taken together they are (C$_3$–C$_4$)alkylene and R$_1$ and R$_4$ are each H.

2. A compound according to claim 1 wherein R is H.

3. A compound according to claim 2 wherein the broken line is no bond.

4. A compound according to claim 3 wherein n is zero or 1.

5. A compound according to claim 4 wherein R$_2$, R$_3$ and R$_4$ are each H and R$_1$ is H, cyclohexyl, C$_6$H$_4$W$_2$ or alk-W$_1$ where alk is (C$_1$–C$_4$)alkylene, ethylidene or isopropylidene; W$_1$ is H, OH, (C$_1$–C$_4$)alkoxy, cyclohexyl or C$_6$H$_4$W$_2$ and W$_2$ is H, F, Cl, Br, CH$_3$ or CH$_3$O.

6. A compound according to claim 5 wherein X is O.

7. A compound according to claim 6 wherein R$_1$ is cyclohexyl, cyclohexylmethyl, benzyl, fluorobenzyl, (C$_1$–C$_4$)alkyl, hydroxymethyl, methoxymethyl or ethoxyethyl.

8. A compound according to claim 7 wherein R$_1$ is benzyl.

9. The compound according to claim 8: 5-[(2-benzyl-2,3-dihydrobenzofuran-5-yl)methyl]thiazolidine-2,4-dione or a sodium salt thereof.

10. The compound according to claim 8: 5-[(2-benzyl-3,4-dihydro-2H-benzopyran-6-yl)methyl]thiazolidine-2,4-dione or a sodium salt thereof.

11. A compound according to claim 4 wherein R$_2$ and R$_3$ taken together form (CH$_2$)$_4$, R$_1$ and R$_4$ are each H and X is O.

12. A compound according to claim 4 wherein R$_1$ and R$_2$ taken together form (CH$_2$)$_5$, R$_3$ and R$_4$ are each H and X is O.

13. A compound according to claim 4 wherein R$_3$ and R$_4$ taken together form (CH$_2$)$_5$, R$_1$ and R$_2$ are each H and X is O.

14. A compound according to claim 5 wherein X is S or

S=O.

15. A compound according to claim 14 wherein n is zero, R$_1$ is H, CH$_3$ or benzyl.

16. A method of lowering the blood glucose in a hyperglycemic mammal which comprises administering to a mammal in need of such treatment a blood glucose lowering effective amount of a compound of claim 1.

17. A method according to claim 16 wherein in said compound of claim 1, R is H and the broken line is no bond.

18. A pharmaceutical composition for use in a hyperglycemic mammal which comprises a blood glucose lowering amount of a compound of claim 1 and a pharmaceutically acceptable carrier.

19. A pharmaceutical composition according to claim 18 wherein in said compound of claim 1, R is H and the broken line is no bond.

* * * * *